(12) United States Patent
Li et al.

(10) Patent No.: US 9,309,268 B2
(45) Date of Patent: Apr. 12, 2016

(54) BORATE MOIETY-CONTAINED LINKER AND BIO-SENSING ELEMENT CONTAINING THE SAME

(71) Applicant: NATIONAL CHIAO TUNG UNIVERSITY, Hsinchu (TW)

(72) Inventors: Yaw-Kuen Li, Hsinchu (TW); Mo-Yuan Shen, Taoyuan County (TW); Yu-Ju Pien, Chiayi (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 14/559,934

(22) Filed: Dec. 4, 2014

(65) Prior Publication Data

US 2015/0094469 A1    Apr. 2, 2015

Related U.S. Application Data

(62) Division of application No. 13/736,087, filed on Jan. 8, 2013, now Pat. No. 8,933,273.

(30) Foreign Application Priority Data

Jun. 27, 2012   (TW) .............................. 101123076 A

(51) Int. Cl.
  *C07F 5/02*    (2006.01)
  *G01N 33/543*  (2006.01)
  *G01N 33/574*  (2006.01)

(52) U.S. Cl.
  CPC .......... *C07F 5/025* (2013.01); *G01N 33/54306* (2013.01); *G01N 33/54353* (2013.01); *G01N 33/574* (2013.01)

(58) Field of Classification Search
  CPC ....................................................... C07F 5/025
  USPC .............................................................. 568/1
  See application file for complete search history.

(56) References Cited

U.S. PATENT DOCUMENTS

| | | |
|---|---|---|
| 6,075,126 A | 6/2000 | Stolowitz et al. |
| 7,208,322 B2 | 4/2007 | Stolowitz et al. |
| 7,629,174 B2 | 12/2009 | Gu |
| 7,989,625 B2 | 8/2011 | Eggenweiler et al. |
| 8,933,273 B2 * | 1/2015 | Li .......................... C07F 5/025 568/1 |
| 2009/0069321 A1 | 3/2009 | Wortmann et al. |

OTHER PUBLICATIONS

Bouriotis et al. Journal of Chromatography (1981), 210(2), 267-78.
Lee et al. Analytical Biochemistry (2002), 310(2), 163-170.

* cited by examiner

*Primary Examiner* — Nizal Chandrakumar
(74) *Attorney, Agent, or Firm* — CKC & Partners Co., Ltd.

(57) ABSTRACT

A borate moiety-contained linker and a bio-sensing element containing the same are disclosed. The borate moiety-contained linker can be used to modify a sensing molecule and connect the sensing molecule to a substrate to form the bio-sensing element.

9 Claims, 3 Drawing Sheets a. Au layer b. 11-MUA-PBA layer c. Anti-PCT/dextran layer d. 1e-13 g/ml PCT e. 1e-12 g/ml PCT f. 1e-11 g/ml PCT g. 1e-10 g/ml PCT h. 1e-9 g/ml PCT

BORATE MOIETY-CONTAINED LINKER AND BIO-SENSING ELEMENT CONTAINING THE SAME

RELATED APPLICATIONS

The present application is a Divisional Application of the application Ser. No. 13/736,087, filed Jan. 8, 2013, the entire contents of which are hereby incorporated herein by reference, which claims priority to Taiwanese Application Serial Number 101123076, filed Jun. 27, 2012, all of which are herein incorporated by reference.

BACKGROUND

1. Technical Field

The present disclosure relates to a sensing material. More particularly, the present disclosure relates to a bio-sensing material.

2. Description of Related Art

Biosensing technologies, which feature high specificity, high sensitivity or high selectivity, promote the development in the field of medical, biomedical testing, environmental engineering, food analysis and biotechnology. The bio-sensing element based on the techniques primarily includes a sensing material and a substrate. The sensing material performs affinity interaction or chemical reaction with a test sample by bioaffinity or chemical catalysis, respectively, to produce or translate signals.

Conventional bio-sensing techniques or elements, such as enzyme-linked immunoassay (ELISA) or commercially available glucose specimen, usually cannot be reused in sample detection and thus is not environmentally friendly. In addition, structures of conventional bio-sensing materials are unstable and the orientations of the specimen under test are inconsistent, which led to poor sensitivity.

SUMMARY

The present disclosure provides a borate moiety-contained linker for JO modifying a sensing molecule and connecting the sensing molecule to a substrate. In this way, biological molecules can be directionally and stably modified on the surface of the substrate, so as to further sensitively perform chemical detection or biological detection.

The linker includes a compound having the following chemical formula (I):

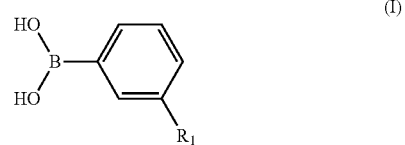

in which $R_1$ is one of the following chemical structures:

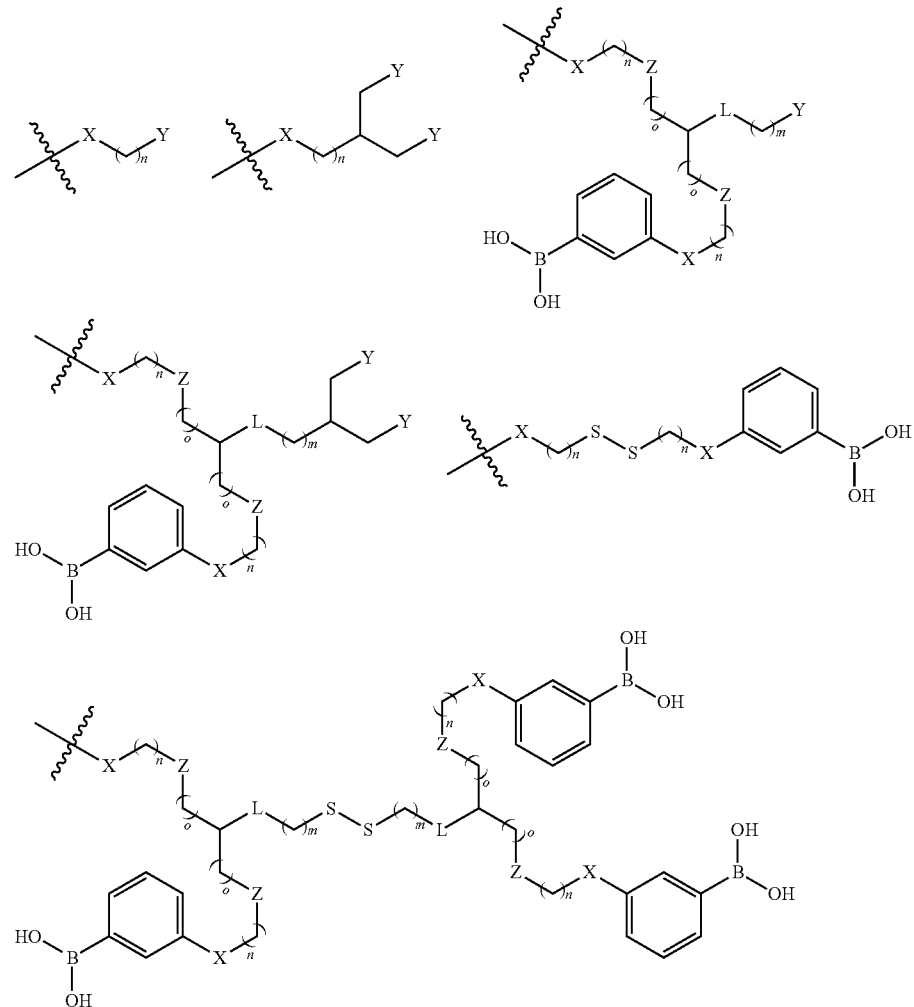

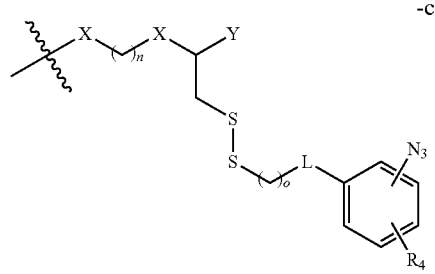
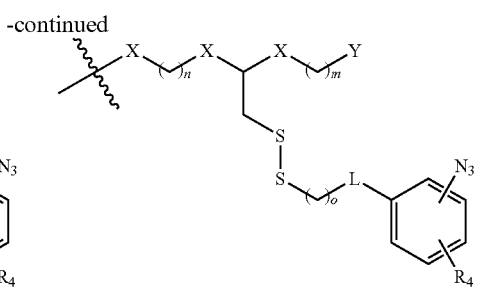

L, X and Z are independently selected the group consisting of amide bond (—CONH— and —NHCO—), ester bond (—COO— and —OCO—), 1,3-succinimide bond

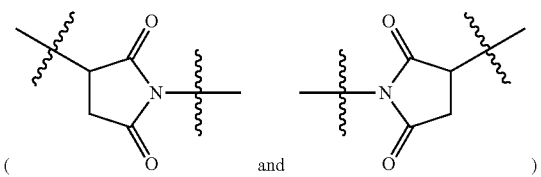

and triazole bond

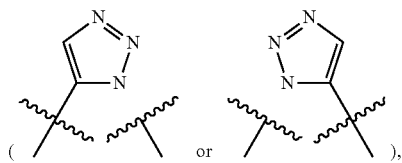

and X, Z and L are different to each other.

Y is thiol group (—SH), amine group (—NH$_2$), azido group (—N$_3$), carboxylic acid group (—COOH) or disulfide-contained group (—S—S—R$_2$). R$_2$ is pyridine

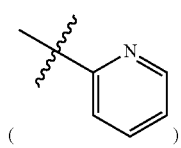 [SMILES: *c1ccccn1]

or 1,2-dithiolane-contained group

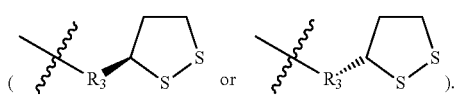

R$_3$ is methylene group (—CH$_2$—) or N-(3H-1,2,3,-triazo)-4-methyl pentanamide

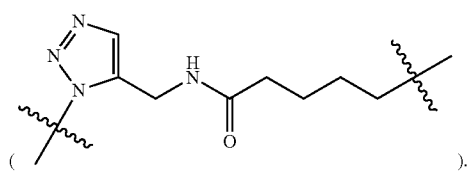 [SMILES: *CCCCC(=O)NCc1cnnn1*]

R$_4$ is hydrogen (H) or nitro group (—NO$_2$).

m is an integral from 1 to 10. n is an integral from 0 to 10. o is 1 or 2.

Further, according to one embodiment of the present disclosure, a bio-sensing element is provided, which includes a substrate and a biomolecular sensing layer connecting thereto. The biomolecular sensing layer includes the borate moiety-contained linker mentioned above.

BRIEF DESCRIPTION OF THE DRAWINGS

The disclosure may be more fully understood by reading the following detailed description of the embodiment, with reference made to the accompanying drawings as follows.

DETAILED DESCRIPTION

Figure 1:
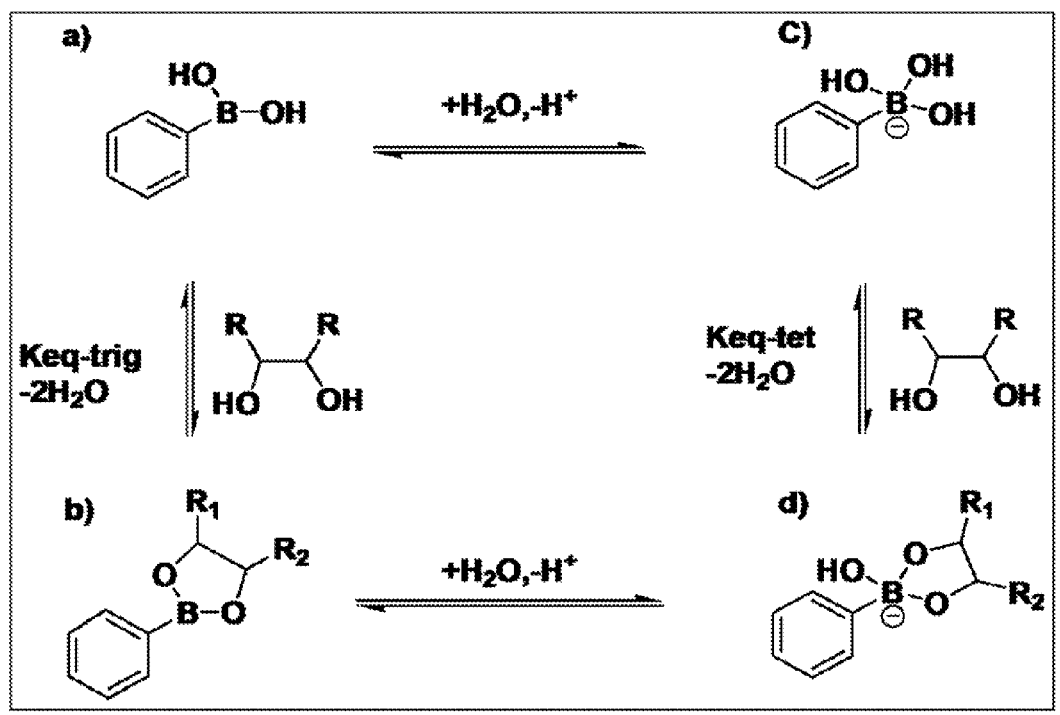
FIG. 1 is a schematic diagram illustrating an action mode between a borate moiety-contained linker and a did molecule according to one embodiment of the present disclosure.

According to one embodiment of the present disclosure, one end of a borate moiety-contained linker contains one or more borate moieties to form covalent bonds with biological molecules. Another end of the linker contains one or more nucleophiles to connect to a surface of a substrate to modify a sensing molecule and connect the sensing molecule to the substrate.

Therefore the borate moiety-contained linker according to the present disclosure can be utilized to let the biological molecules be directionally and stably modified on the surface of the substrate, so as to sensitively perform chemical detection or biological detection. Further, the biological molecules, which bonds to the borate moiety, can be desorbed and then removed to regenerate the sensing material or the element.

The present disclosure is described by the following specific embodiments. Those with ordinary skill in the arts can readily understand the other advantages and functions of the present disclosure after reading the disclosure of this specification. Various details described in this specification can be modified based on different viewpoints and applications without departing from the scope of the present disclosure.

Borate Moiety-Contained Linker

The present disclosure provides a borate moiety-contained linker and a method for manufacturing the same. The borate moiety-contained linker has a structure represented by the following chemical formula (I):

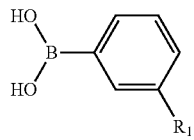

(I)

in which $R_1$ is one of the following chemical structures:

L, X and Z are independently selected from the group consisting of amide bond (—CONH— and —NHCO—), ester bond (—COO— and —OCO—), 1,3-succinimide bond

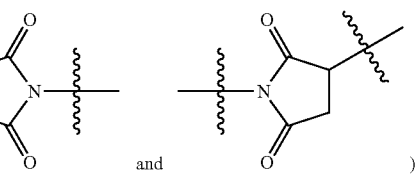

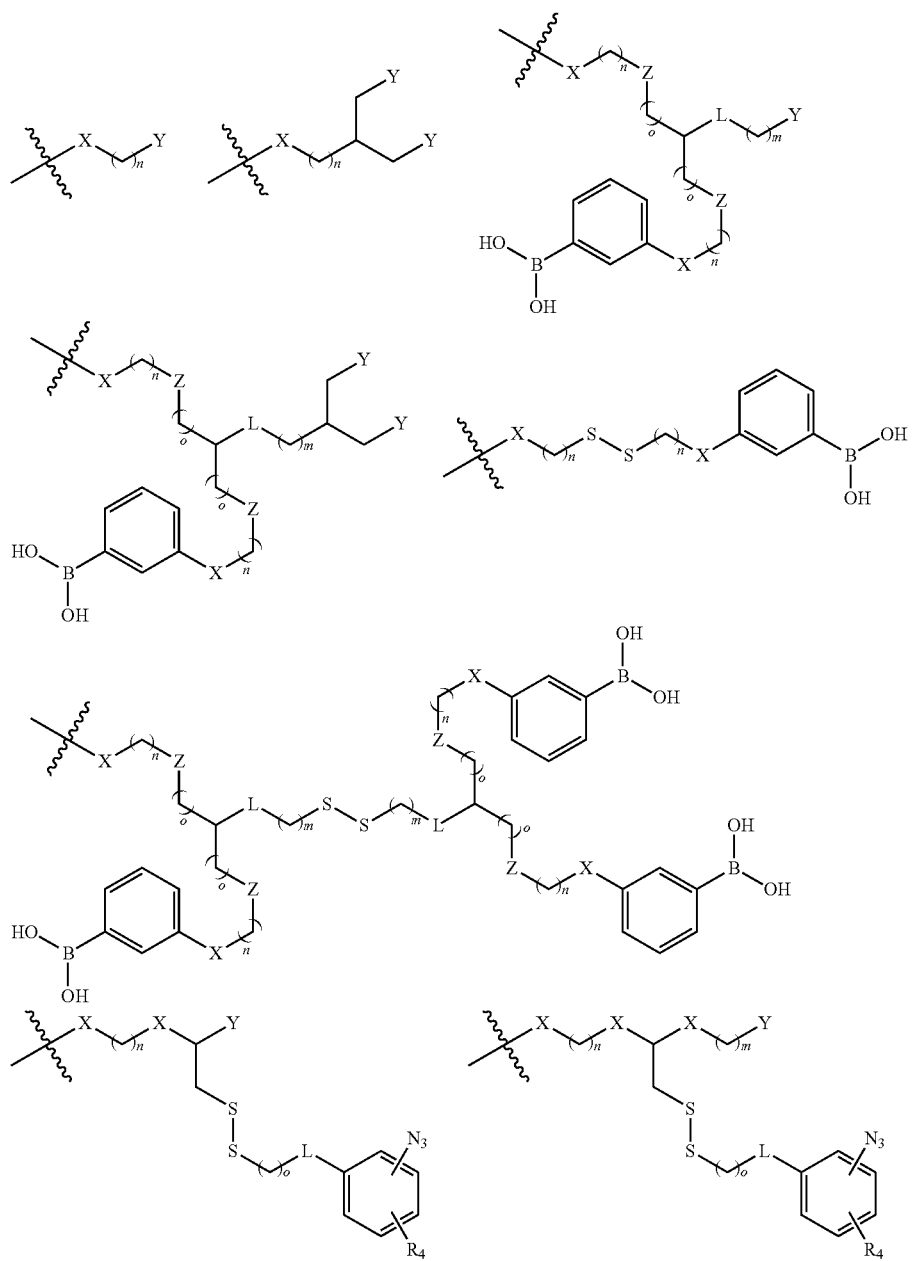

or triazole bond

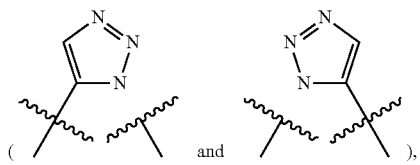

and X, Z and L are different to each other.

Y is thiol group (—SH), amine group (—NH$_2$), azido group (—N$_3$), carboxylic acid group (—COOH) or disulfide-contained group (—S—S—R$_2$).

R$_2$ is pyridine

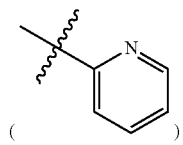 [SMILES: *c1ccccn1]

or 1,2-dithiolane-contained group

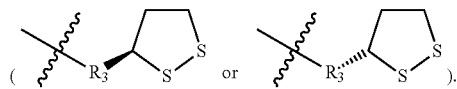

R$_3$ is methylene group (—CH$_2$—) or N-(3H-1,2,3,-triazo)-4-methyl pentanamide

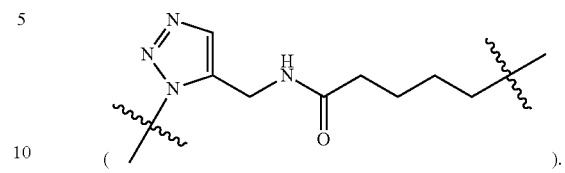

R$_4$ is hydrogen (H) or nitro group (—NO$_2$).

m is an integral from 1 to 10. n is an integral from 0 to 10. o is 1 or 2.

EXAMPLE 1

Borate Moiety-Contained Linker MB1

MB1 and a method for fabricating the same are provided. MB1 may be used as a bio-sensing material, but not limited thereto. MB1 has a structure represented by the following chemical formula:

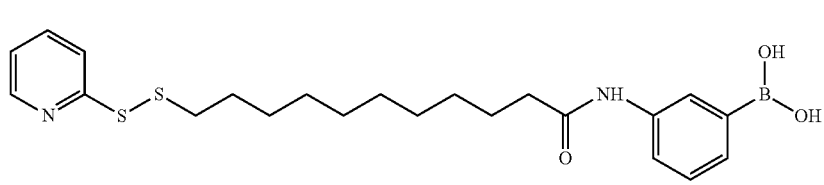

According to one embodiment of the present disclosure, the method for manufacturing MB1 includes performing thiol substitution reaction, disulfide replacement reaction and amide coupling reaction. By the reactions mentioned above, the borate moiety-contained linker MB1 can be obtained.

Scheme 1

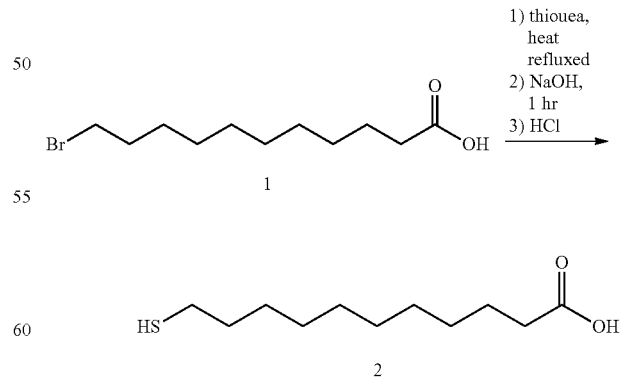

In thiol substitution reaction (as shown in Scheme 1), 11-bromoundecanoic acid (1) and thiourea perform substitution reaction, and thus thiol group (—SH) substitutes bromine group (—Br) to form 11-mercaptoundecanoic acid (2).

Scheme 2

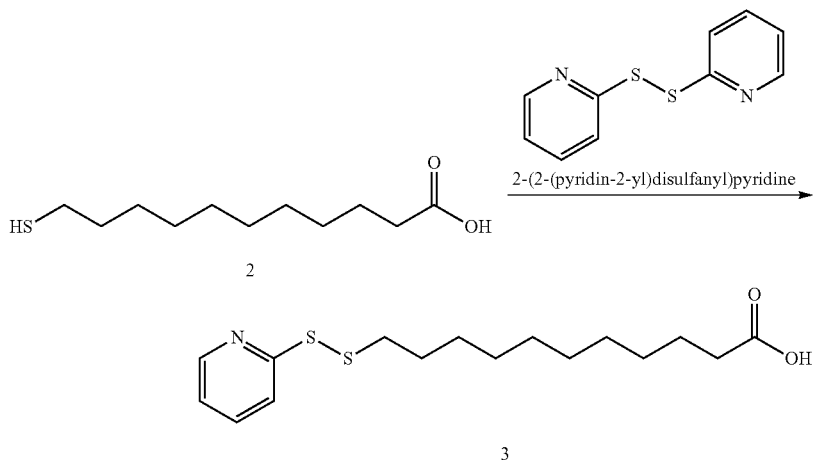

In disulfide replacement reaction (as shown in Scheme 2), 11-mercaptoundecanoic acid (2) and 2-(2-(pyridin-2-yl)disulfanyl)pyridine perform substitution reaction to form 11-(2-(pyridin-2-yl)disulfanyl)undecanoic acid (3) containing a disulfide bond of a reduced state.

Scheme 3

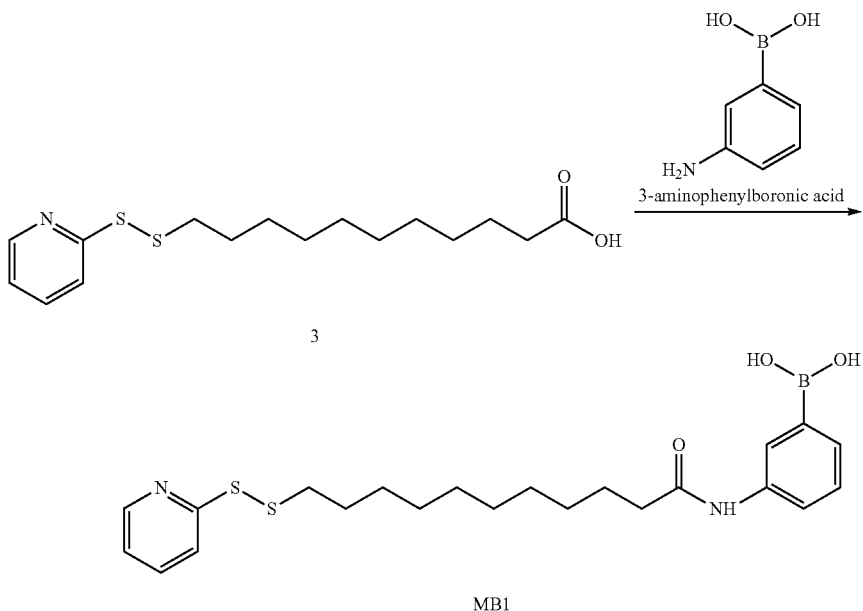

In amide bond coupling reaction (as shown in Scheme 3), 11-(2-(pyridin-2-yl)disulfanyl)undecanoic acid (3) and 3-aminophenylboronic acid perform coupling reaction to form MB1 containing the borate moiety.

EXAMPLE 2

Borate Moiety-Contained Linker MB2

MB2 and a method for fabricating the same are provided. MB2 may be used as a bio-sensing material, but not limited thereto. MB2 has a structure represented by the following chemical formula:

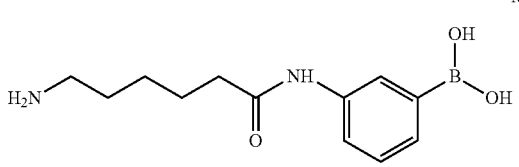

According to one embodiment of the present disclosure, the method for manufacturing MB2 includes performing azide substitution reaction, amide coupling reaction and hydrogenation. By the reactions mentioned above, the borate moiety-contained linker MB2 can be obtained.

Scheme 4

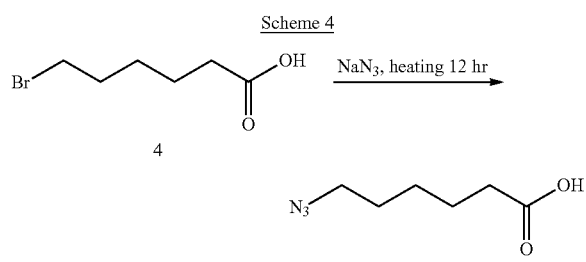

In azide substitution reaction (as shown in Scheme 4), 6-bromohexanoic acid (4) and sodium azide (NaN₃) perform substitution reaction, and thus azido group (—N₃) substitutes bromine group (—Br) to form 6-azidohexanoic acid (5).

Scheme 5

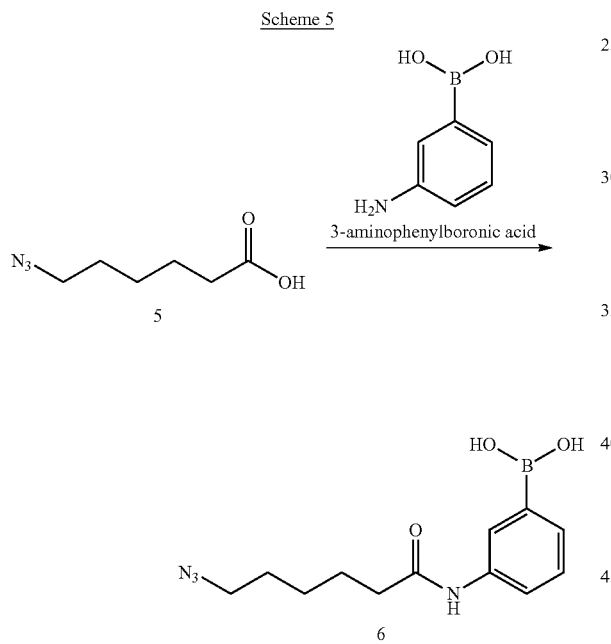

In amide coupling reaction (as shown in Scheme 5), 6-azidohexanoic acid (5) and 3-aminophenylboronic acid perform coupling reaction to form 3-(6-azidohexanamido)phenylboronic acid (6) containing the borate moiety.

Scheme 6

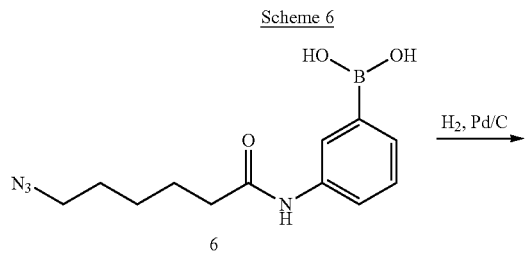

-continued

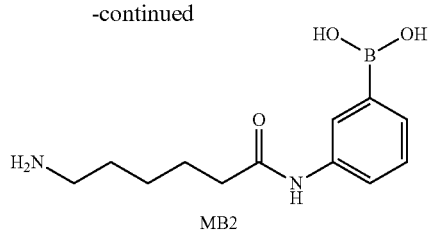

MB2

In hydrogenation reaction (as shown in Scheme 6), 3-(6-azidohexanamido)phenylboronic acid (6) and hydrogen perform oxidation and reduction reaction under the catalyzation of Pd/C to reduce azido group to amine group (—NH₂), so as to form MB2 containing an amine group.

EXAMPLE 3

Borate Moiety-Contained Linker DB1

DB1 and a method for fabricating the same are provided. DB1 may be used as a bio-sensing material, but not limited thereto. DB1 has a structure represented by the following chemical formula:

DB1

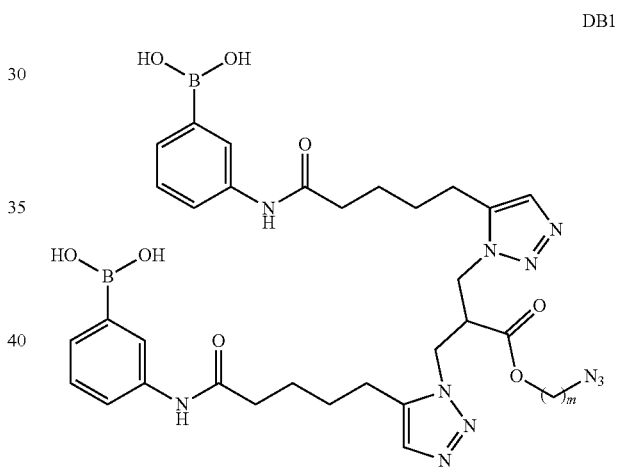

According to one embodiment of the present disclosure, the method for manufacturing DB1 includes performing azide substitution reaction, click reaction and esterification reaction. By the reactions mentioned above, the borate moiety-contained linker DB1 can be obtained.

Scheme 7

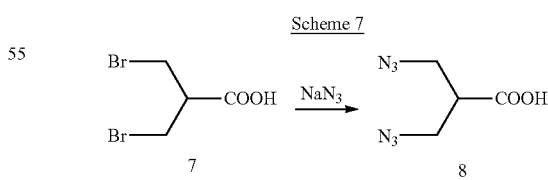

In azide substitution reaction (as shown in Scheme 7), 3-bromo-2-(bromomethyl)propanoic acid (7) and sodium azide (NaN₃) perform substitution reaction, and thus azido group (—N₃) substitutes bromine group (—Br) to form 3-azido-2-(azidomethyl)propanoic acid (8) containing two azido groups.

Scheme 8

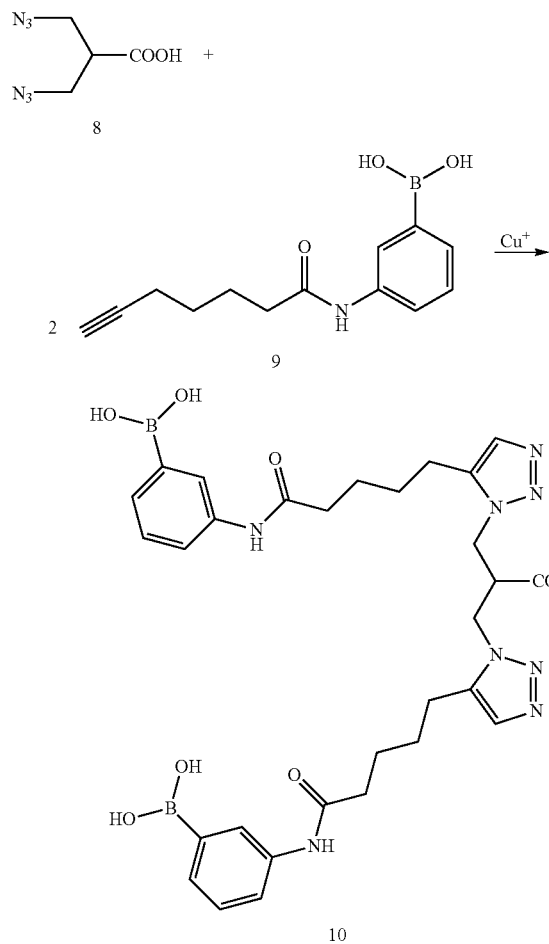

Scheme 9

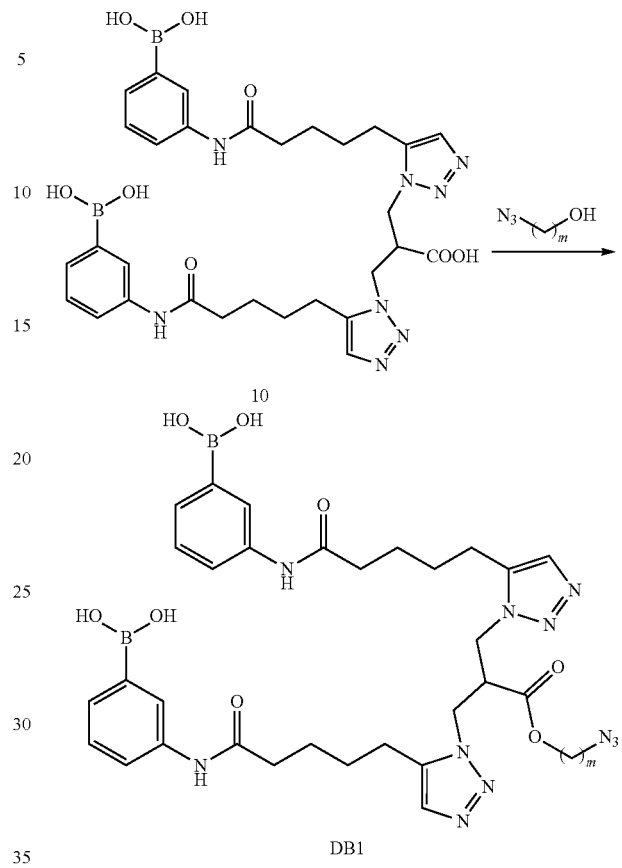

In click reaction (as shown in Scheme 8), 3-azido-2-(azidomethyl)propanoic acid (8) and 3-hept-8-ynamidophenyl-boronic acid (9) perform click reaction under the catalyzation of cuprous ions (Cu⁺) to form a first intermediate (10) containing two borate moieties.

In esterification reaction (as shown in Scheme 9), the first intermediate (10) and azido alkyl alcohol perform esterification reaction to form DB1 containing two borate moieties. In the structure of DB1, m is an integral from 1 to 10.

EXAMPLE 4
Borate Moiety-Contained Linker DB2

DB2 and a method for fabricating the same are provided. DB2 may be used as a bio-sensing material, but not limited thereto. DB2 has a structure represented by the following chemical formula:

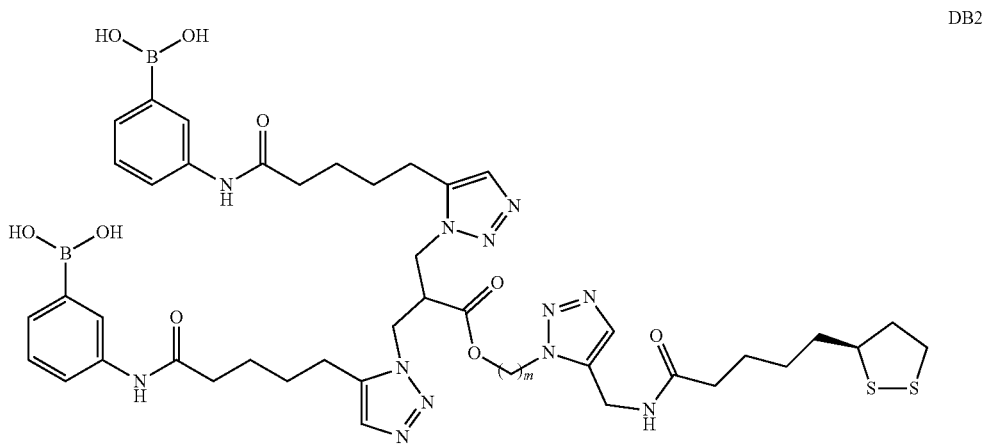

According to one embodiment of the present disclosure, the method for manufacturing DB2 includes performing amide coupling reaction and click reaction. By the reactions mentioned above, the borate moiety-contained linker DB2 can be obtained.

In click reaction (as shown in Scheme 11), DB1 and (S)-5-(1,2-dithiolan-3-yl)-N-(prop-2-ynyl)pentanamide (12) perform click reaction under catalyzation of cuprous ions to form DB2 containing a 1,2-dithiolane group.

EXAMPLE 5

Borate Moiety-Contained Linker DB3

DB3 and a method for fabricating the same are provided. DB3 may be used as a bio-sensing material, but not limited thereto. DB3 has a structure represented by the following chemical formula:

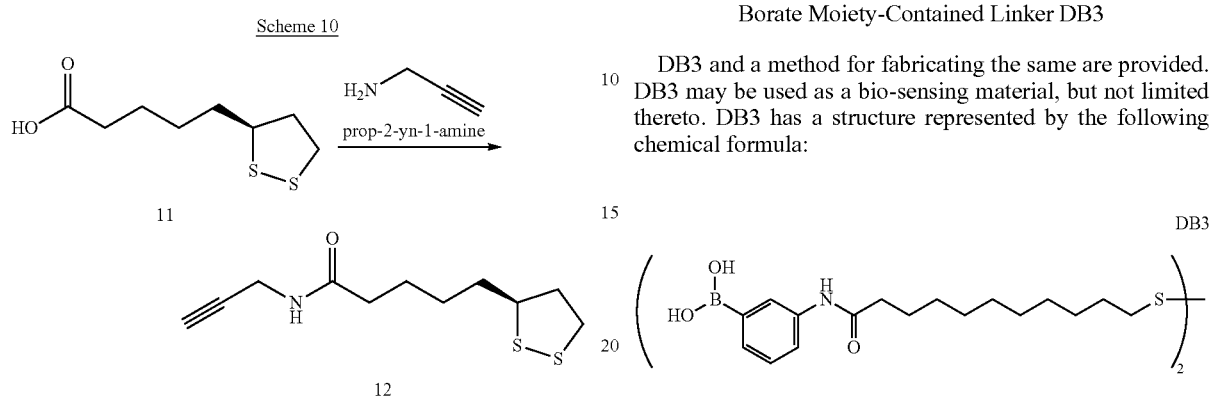

In amide coupling reaction (as shown in Scheme 10), (S)-5-(1,2-dithiolan-3-yl)pentanoic acid (11) and prop-2-yn-1-amine perform coupling reaction to form (S)-5-(1,2-dithiolan-3-yl)-N-(prop-2-ynyl)pentanamide (12).

According to one embodiment of the present disclosure, the method for manufacturing DB3 includes performing disulfide polymerization and amide coupling reaction. By the reactions mentioned above, the borate moiety-contained linker DB3 can be obtained.

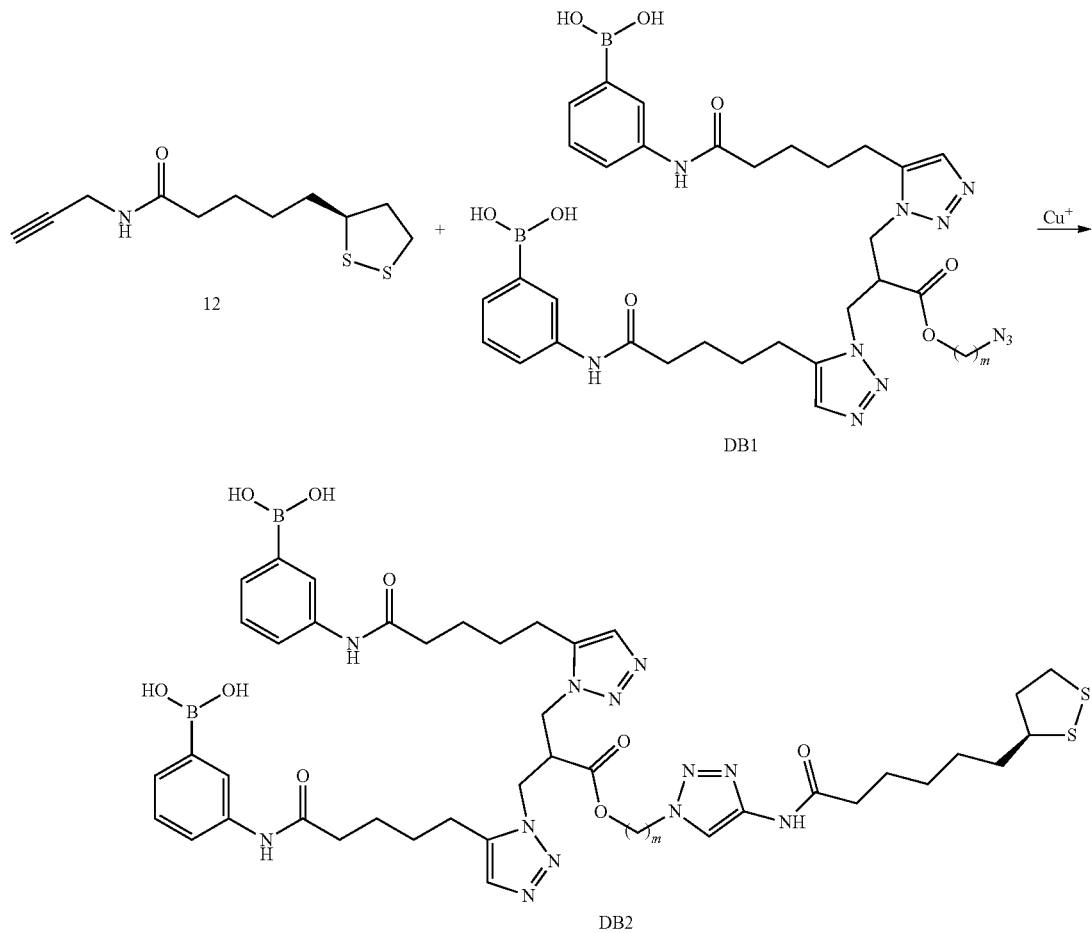

Scheme 12

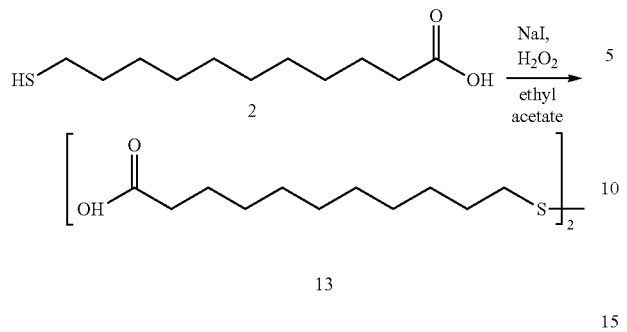

In dimer polymerization (as shown in Scheme 12), 11-mercaptoundecanoic acid (2) and hydrogen peroxide ($H_2O_2$) perform dimer polymerization to form a second intermediate (13) containing a disulfide bond.

Scheme 13

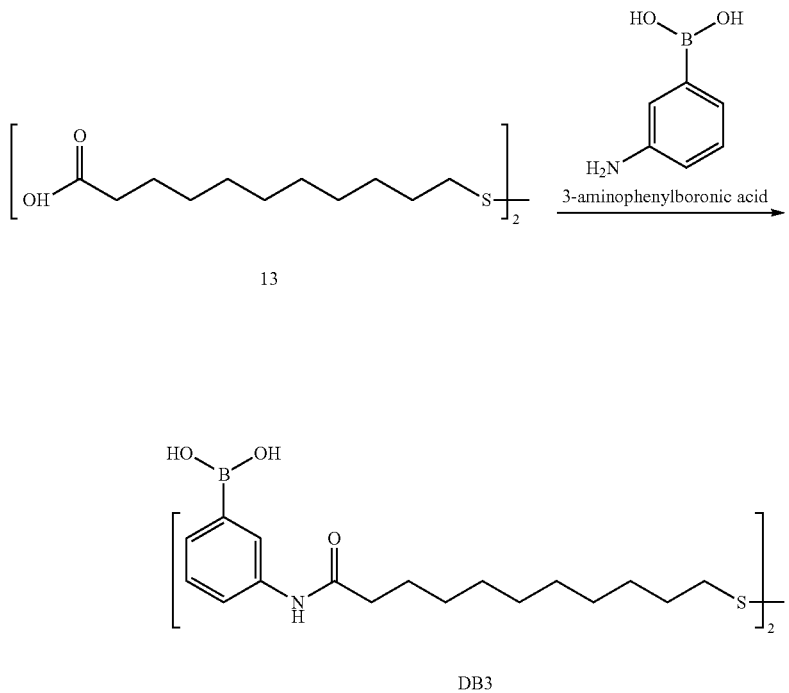

In amide coupling reaction (as shown in Scheme 13), the second intermediate (13) and 3-aminophenylboronic acid perform coupling reaction to form DB3 (in the form of dimer).

EXAMPLE 6

Borate Moiety-Contained Linker TB1

TB1 and a method for fabricating the same are provided. TB1 may be used as a bio-sensing material, but not limited thereto, TB1 has a structure represented by the following chemical formula:

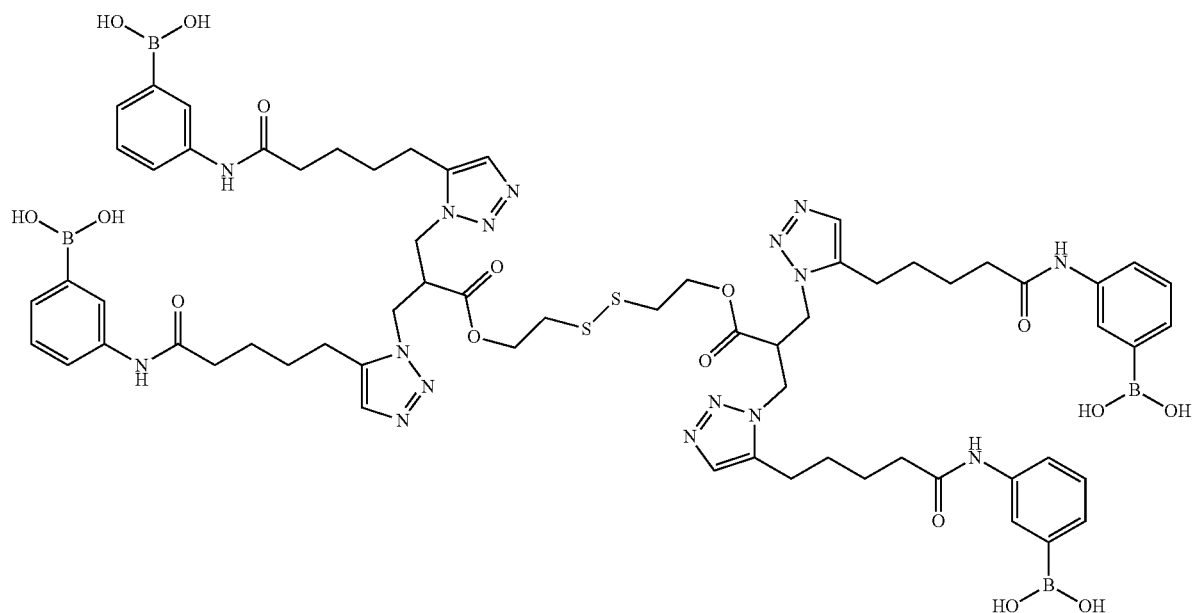
TB1
According to one embodiment of the present disclosure, TB1 can be obtained by employing esterification reaction.
Scheme 14
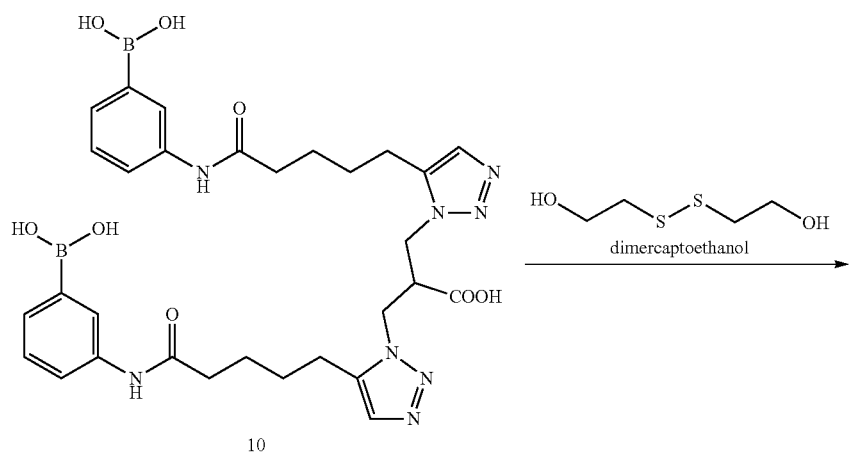

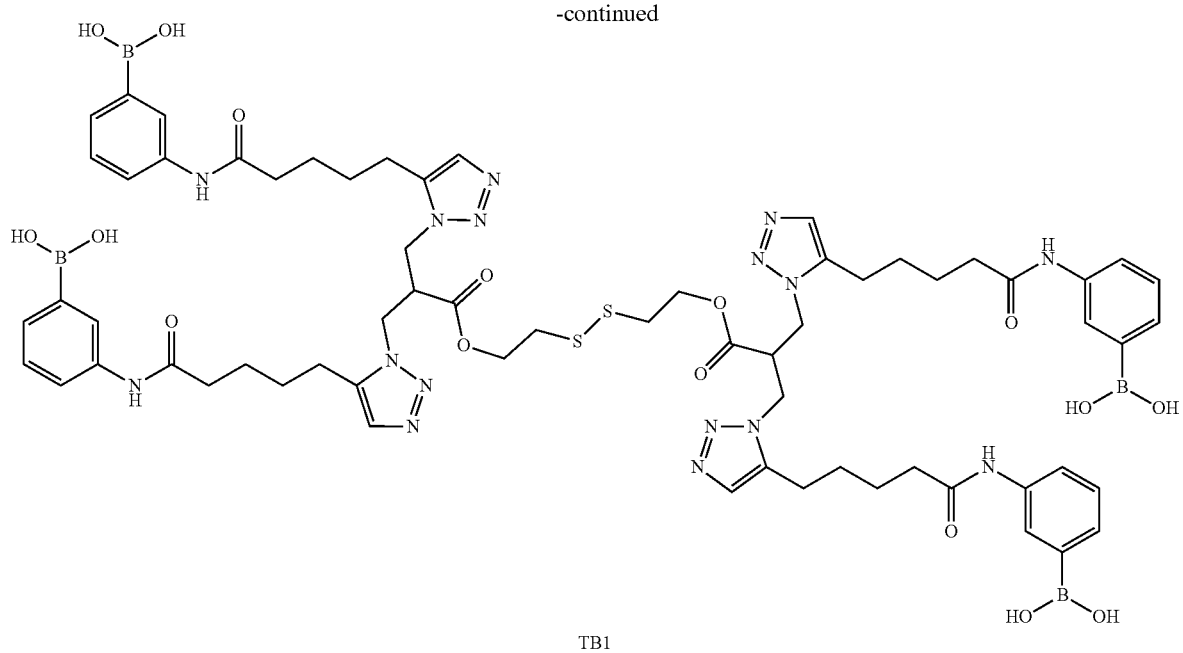

TB1

In esterification reaction (as shown in Scheme 14), the first intermediate (10) and dimercaptoethanol perform esterification to form TB1 containing four borate moieties.

EXAMPLE 7

Borate Moiety-Contained Linker MBA1

MBA1 and a method for fabricating the same are provided. MBA1 may be used as a bio-sensing material, but not limited thereto. MBA1 has a structure represented by the following chemical formula:

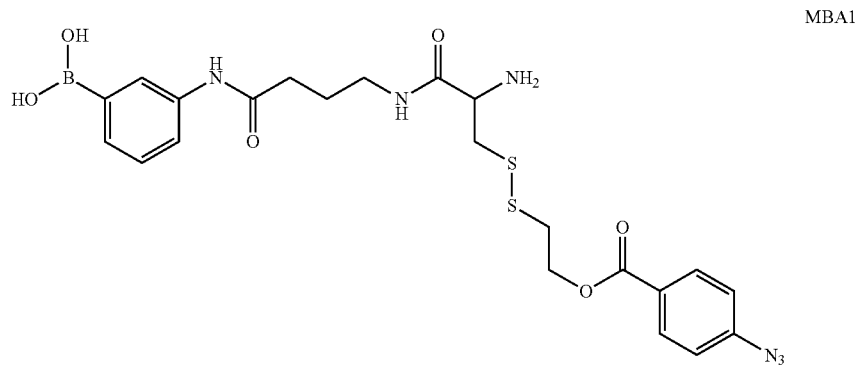 [SMILES: [N-]=[N+]=Nc1ccc(C(=O)OCCSSCC(N)C(=O)NCCCC(=O)Nc2cccc(B(O)O)c2)cc1]

MBA1

According to one embodiment of the present disclosure, a method for manufacturing MBA1 includes preparing azido initial compound, performing a first amide coupling reaction, a first amine ester bond hydrolysis reaction, a second amide coupling reaction, disulfide reduction reaction, disulfide substitution reaction and a second amine ester bond hydrolysis reaction. By the reactions mentioned above, a borate moiety-contained linker MBA1 can be obtained.

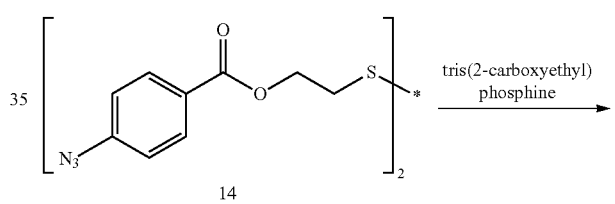

Scheme 15

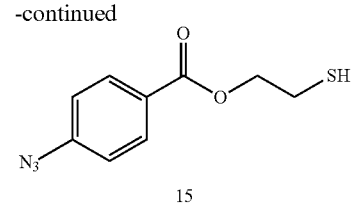

-continued

15

-continued

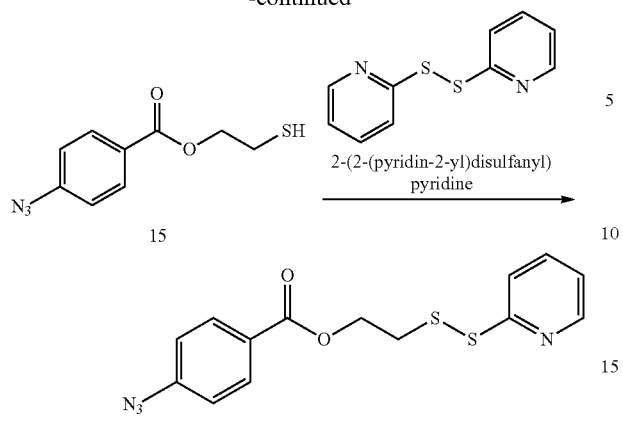

In the step of preparing the azido initial compound (as shown in scheme 15), first, an azido reactant (14) performs disulfide bond reduction reaction by tris(2-carboxyethyl) phosphine (TCEP) to form a third intermediate (15) containing a thioether bond. Sequentially, the thirdintermediate (15) performs disulfide substitution reaction by 2-(2-(pyridin-2-yl)disulfanyl)pyridine to form the azido initial compound (16) containing a disulfide bond.

Scheme 16

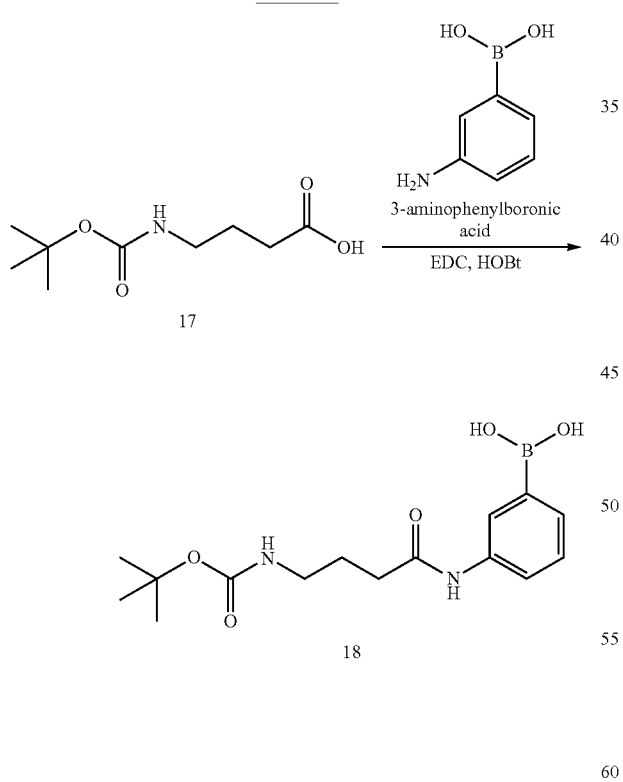

In the first amide coupling reaction (as shown in Scheme 16), a first amine ester reactant (17) and 3-aminophenylboronic acid perform amide bond coupling reaction by N-ethyl-N'(3-dimethylaminopropyl)carbodiimide (EDC) and 1-hydroxybenzptriazole (HOBt) to form a fourth intermediate (18) containing an amine ester bond.

Scheme 17

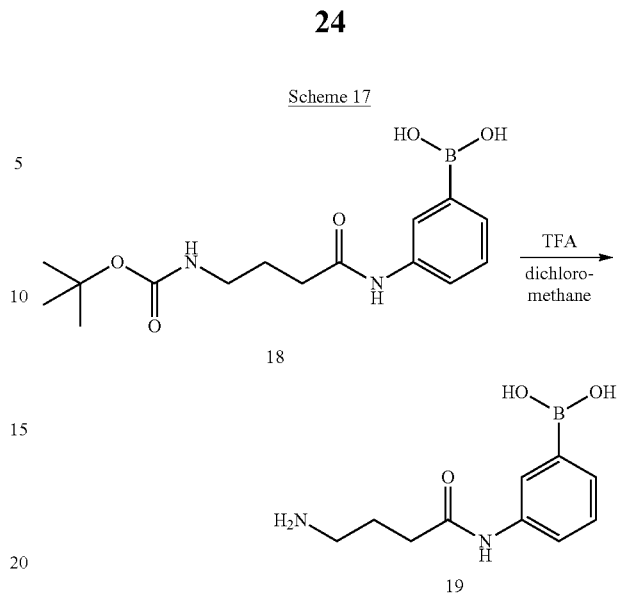

In the first amine ester hydrolysis reaction (as shown Scheme 17), the fourth intermediate (18) performs amine ester hydrolysis reaction by trifluoracetic acid (TFA) to form a fifth intermediate (19) containing an amine group.

In the second amide bond coupling reaction (as shown in Scheme 18), the fifth intermediate (19) and a disulfide reactant (20) perform amide coupling reaction to form a sixth intermediate (21) containing a disulfide bond.

Scheme 19

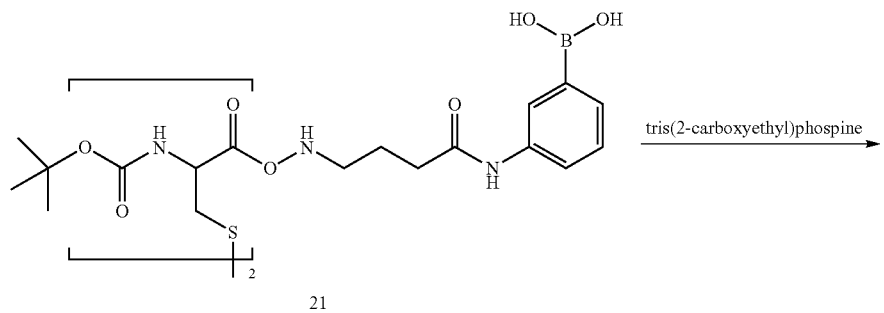

21

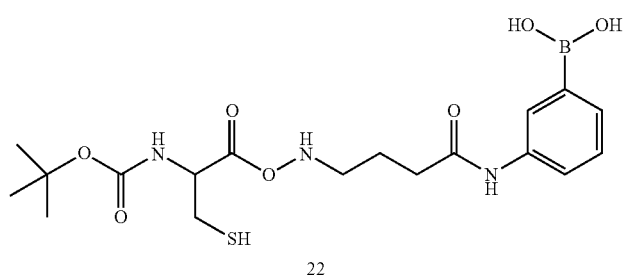

22

In disulfide reduction reaction (as shown in Scheme 19), the sixth intermediate (21) performs disulfide bond reduction reaction by tris(2-carboxyethyl)phosphine (TCEP) to form a seventh intermediate (22) containing a thioether bond.

Scheme 20

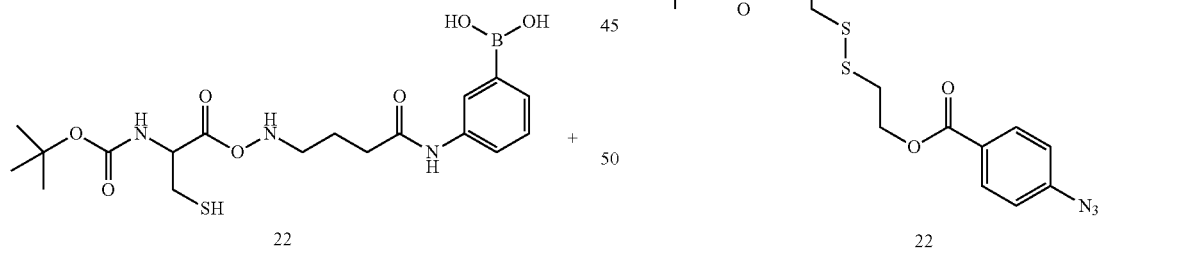

22

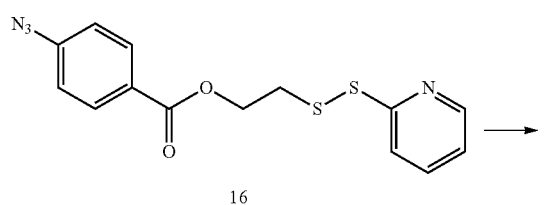

16

-continued

22

In the disulfide substitution reaction (as shown in Scheme 20), the seventh intermediate (22) and the azido initial compound (16) perform disulfide substitution reaction to form an eighth intermediate (23) containing a thioether bond.

Scheme 21

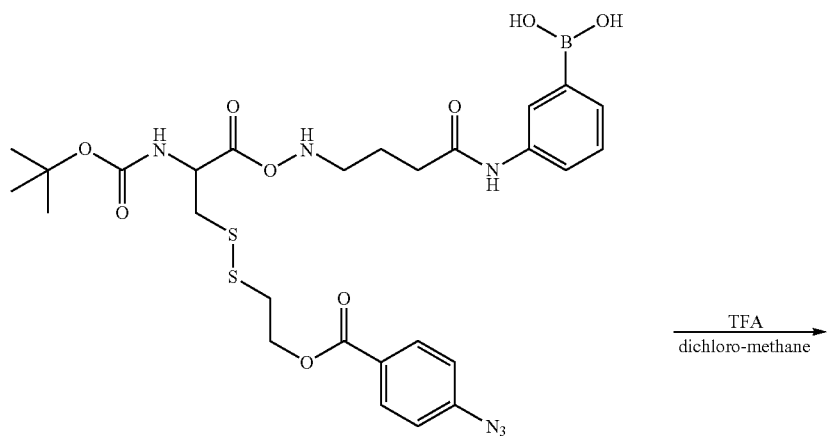

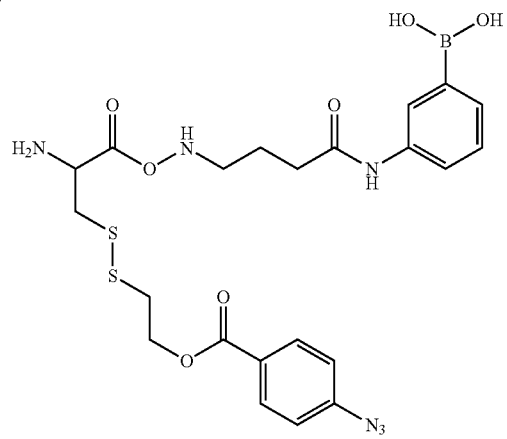

In the second amine ester bond hydrolysis reaction (as shown in Scheme 21), the eighth intermediate (23) performs amine ester bond hydrolysis reaction to form MBA1 containing an azido group.

EXAMPLE 8
Borate Moiety-Contained Linker MBA2

MBA2 and a method for fabricating the same are provided. MBA2 may be used as a bio-sensing material, but not limited thereto. MBA2 has a structure represented by the following chemical formula:

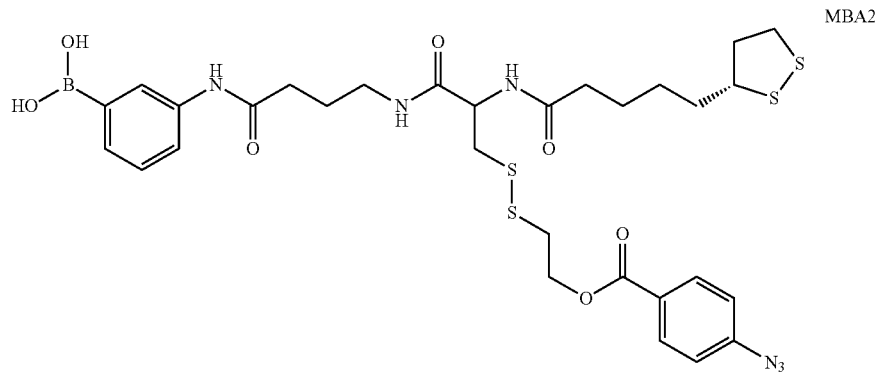 [SMILES: [N-]=[N+]=Nc1ccc(C(=O)OCCSSCC(NC(=O)CCCC[C@@H]2CCSS2)C(=O)NCCCC(=O)Nc2cccc(B(O)O)c2)cc1]

According to one embodiment of the present disclosure, a borate moiety-contained linker MBA2 can be obtained by employing amide coupling reaction.

Scheme 22

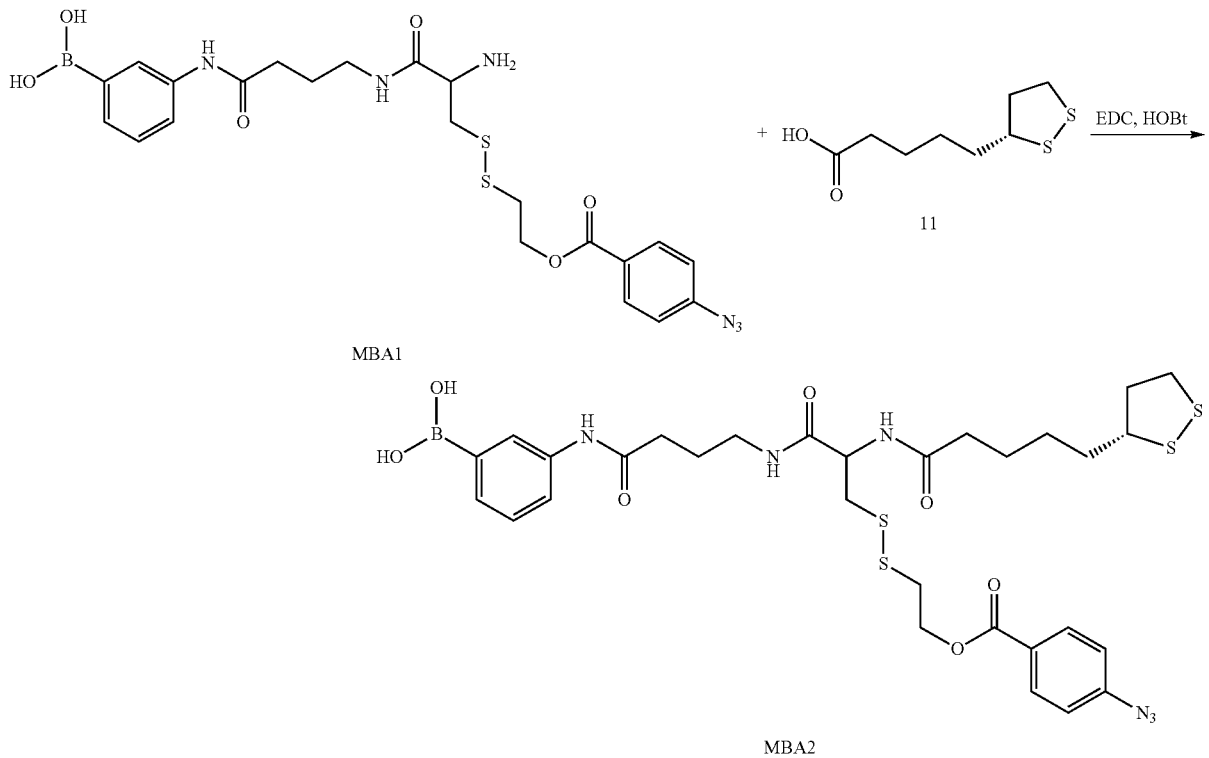

In the amide coupling reaction, MBA1 containing the amino group and (S)-5-(1,2-dithiolan-3-yl)pentanoic acid (11) perform amide coupling reaction by EDC and HOBt to form MBA2 containing an azido group.

Application to Borate Moiety-Contained Linker of Bio-Sensing Element

The borate moiety-contained linker can be utilized as a sensing material of a bio-sensing element. In the embodiments hereinafter, the linkers mentioned above are applied to detect contents of a specific molecule in testing samples.

Reactive Principle

The reaction between the borate moiety of the borate moiety-contained linker and a diol molecule is shown in FIG. 1. According to $K_{eq\text{-}trig}$, the borate moiety (a shown in FIG. 1) and the diol molecule can dehydrate under a neutral condition to form a three-coordinate covalent product (b shown in FIG. 1). The three-coordinate covalent product (b shown in FIG. 1) can form a four-coordinate covalent product (d shown in FIG. 1) under a basic condition.

Further, according to $K_{eq\text{-}tert}$, under a basic condition, the boron atom of the borate group (a shown in FIG. 1) forms a four-coordinate structure (c shown in FIG. 1). The four-coordinate borate moiety-contained linker and the diol group dehydrate to form a four-coordinate covalent product (d shown in FIG. 1).

According to one embodiment of the present disclosure, in a pH range of 7 to 10, the borate group and an alcohol group can form stable covalent bond. In contrast, under an acidic condition, the pH value less than 6, the borate moiety of the borate moiety-contained linker connecting to the alcohol group desorbs the alcohol group to regenerate the borate moiety-contained linker. In other words, the borate moiety-contained linker can reuse by employing acidification regeneration.

Reactive Mode

The borate group of the borate moiety-contained linker able to react with various alcohol-contained molecules to form covalent bond is already known. Among them, diol group-contained biological molecules, such as protein, nucleic acid and sugar, exhibit better reactivity.

For instance, antibodies have been widely used in biomedical testing to provide specificity of screening for many diseases and cancers. The past is known; a crystalizable fragment (Fc) of the antibody exhibits a phenomenon of glycosylation, and the carbohydrate group has many vicinal diol groups able to react with borate moiety to form a covalent bond. Compared to affinity interaction of the biological molecules, the antibody can stably bind the borate moiety-contained linker to form a stable structure by a covalent bond.

Because the reactive orientations between a conventional bo-sensing material and an antibody are not consistent, the identification region ($F_{ab}$) of the antibody cannot effectively contact a testing sample, so as to decrease detection sensitivity. When the orientation of the antibody is vertical and back to the substrate, the antibody exhibits better detection sensitivity. In contrast, when the orientation of the antibody is parallel or toward the substrate, detection sensitivity thereof decreases or the antibody exhibits no effect.

Figure 2:
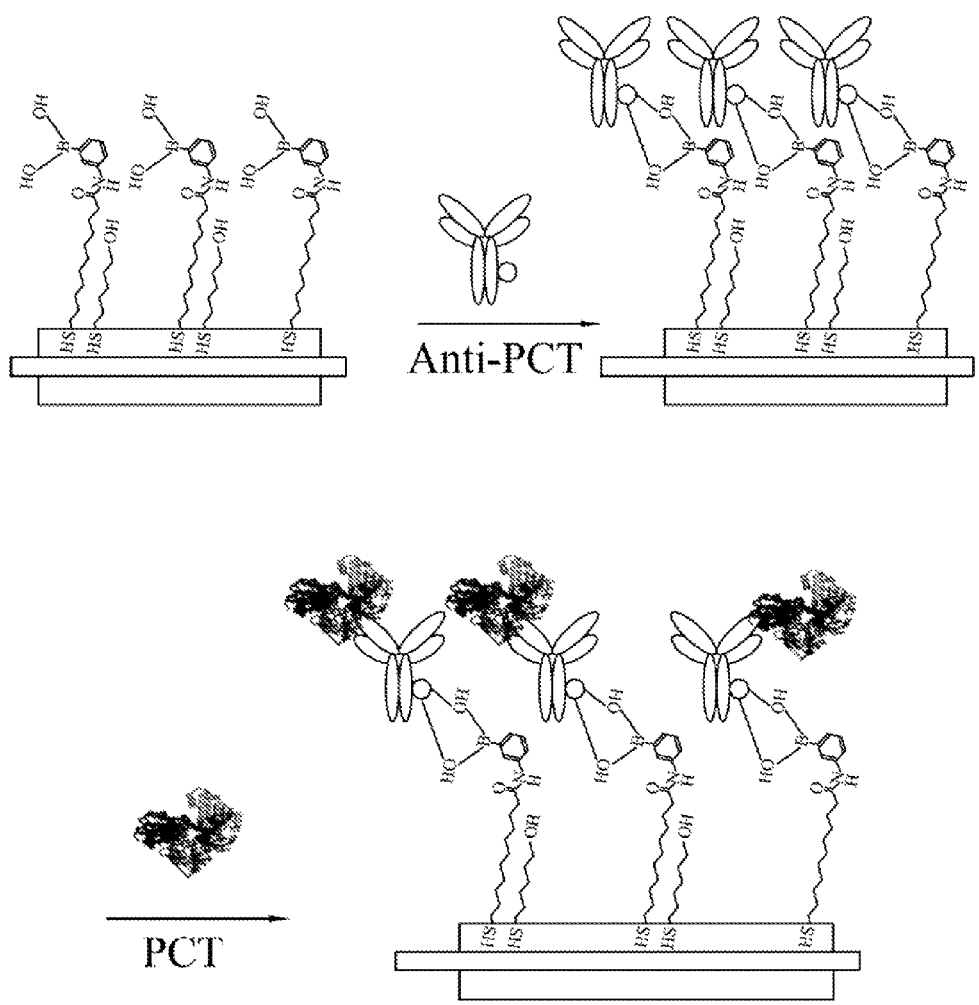
FIG. 2 is a cartoon diagram illustrating reactive orientation between a borate moiety-contained linker and procalcitonin antibody according to one embodiment of the present disclosure.

The reactive orientations of both the borate moiety-contained linker, disclosed in the present disclosure, and anti-procalcitonin (anti-PCT) are shown in FIG. 2. Thiol group (—SH), amine group (—NH$_2$), azido group (—N$_3$) or carboxylic acid group (—COOH) of one end of the borate moiety-contained linker can respectively perform coupling reaction with thiopyridine group, carboxylic acid group (—COOH), alkynyl group (—C≡C) or amine group (—NH$_2$) of a surface of a silicon chip to form a biomolecular sensing layer. Alternatively, thiol group (—SH) of one end of the borate moiety-contained linker can perform self-assembly reaction with a surface of a metal chip to form a biomolecular sensing layer.

The borate moiety-contained linker contains a long carbon chain and the borate moiety, and thus the antibody is vertical and back to the substrate when the antibody reacts with the linker. Thus, the identification regions of the antibodies can effectively contact the test samples. In other words, the orientations of the antibodies binding to the linkers exhibit consistency, and thus the antibodies can effectively contact the procalcitonin (POT) to further increase detection sensitivity of the antibodies.

Furthermore, the borate moiety-contained linker further includes a photo-activating group, which can perform photochemical reaction with a biological molecule containing a specific group to form a chemical bond by absorbing energy of a specific wavelength. The photo-activating group may be azide phenyl group

Figure 3:
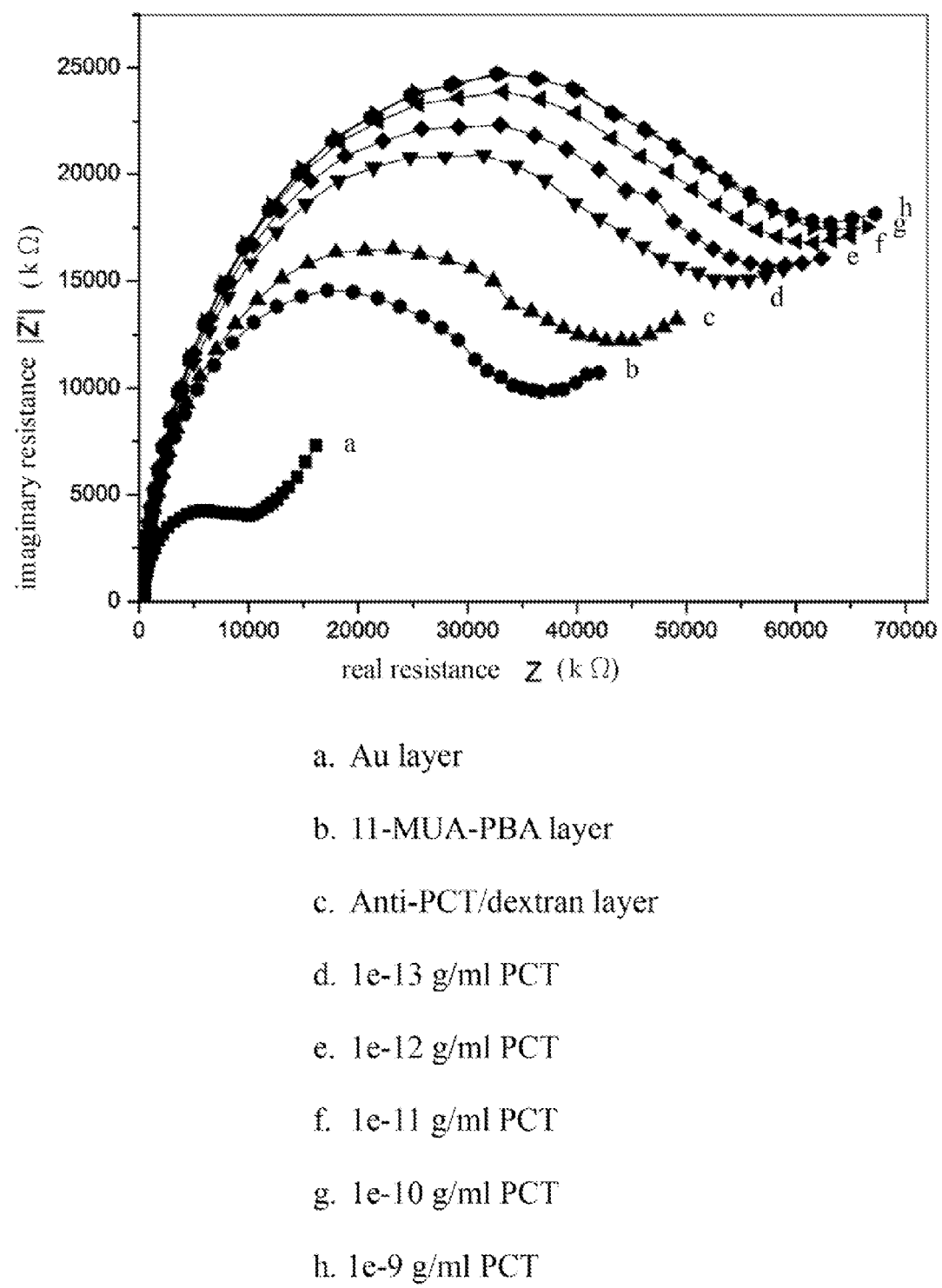
FIG. 3 is a curve diagram related to procalcitonin antibody (anti-PCT) binding to a borate moiety-contained linker and procalcitonin (PCT) with different concentrations. The x axis is real resistance (kΩ), and y axis is imaginary resistance (kΩ). (a) Au layer, (b) 11-MUA-PBA layer, (c) Anti-PCT/dextran layer, (d) with 1e-13 g/ml PCT, (e) with 1e-12 g/ml PCT, (f) with 1e-11 g/ml PCT, (g) with 1e-10 g/ml PCT, (h) with 1e-19 g/ml PCT.

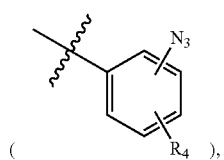

but not limited thereto. R$_4$ is an electrophile group to increase reactivity of the azido group. According to another embodiment of the present disclosure, R$_4$ is a nitro group (—NO$_2$), FIG. 3 is a curve diagram related to procalcitonin antibody (anti-POT) binding to the borate moiety-contained linker and procalcitonin (PCT) with different concentrations. According to one embodiment of the present disclosure, the anti-PCT binding to the borate moiety-contained linker is disposed on a gold chip. A quartz crystal microbalance (QCM) is used to detect standard samples of PCT with different concentrations. By the experimental results, the detection limits can be achieved to 10 pg/ml, but the conventional detection limits is about 1 ng/ml.

As mentioned above, the borate moiety-contained linker can bind to various kinds of alcohol-contained biological molecules, especially the biological molecules containing diol group and exhibiting better reactivity. After testing, an acidification process can be employed to desorb the alcohol group to regenerate the borate moiety-contained linker. Moreover, the borate moiety-contained linker and a biological molecule can form a covalent bond to form a stable structure. Also, the orientations of the biological molecules binding to the linkers exhibit consistency to further increase sensitivity of chemical or biological detection.

Although the present disclosure has been described in considerable detail with reference to certain embodiments thereof, other embodiments are possible. Therefore, the spirit and scope of the appended claims should not be limited to the description of the embodiments contained herein.

It will be apparent to those ordinarily skilled in the art that various modifications and variations may be made to the structure of the present disclosure without departing from the scope or spirit of the disclosure. In view of the foregoing, it is intended that the present disclosure cover modifications and variations thereof provided they fail within the scope of the following claims.

What is claimed is:

1. A borate moiety-contained linker for modifying a sensing molecule and connecting the sensing molecule to a substrate, the linker comprising a compound having a structure represented by the following chemical formula (I):

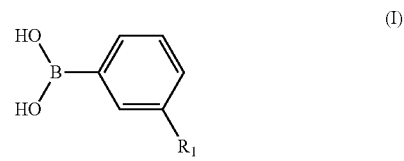

wherein

R$_1$ is one of the following chemical structures:

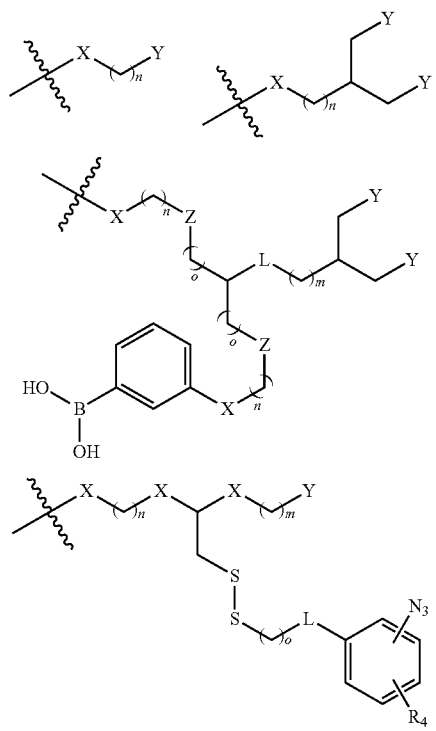

X is selected from the group consisting of ester bond (—COO— and —OCO—), 1,3-sucinimide bond

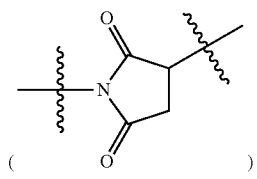 [SMILES: *C1CC(=O)N(*)C1=O]

and triazole bond

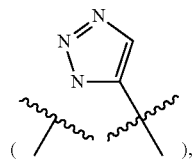

and

L is ester bond (—COO— and —OCO—), and

Z is selected from the group consisting of amide bond (—CONH— and —NHCO—) ester bond (—COO— and —OCO—), 1,3-succinimide bond

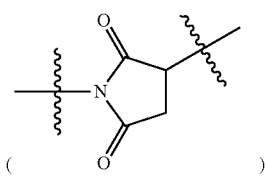

and triazole bond

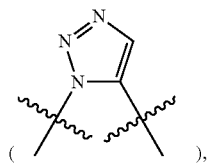 [SMILES: *c1cnnn1*]

and X, Z and L are different to each other, when X is the 1,3-succinimide bond or the triazoie bond, N atom of the 1,3-succinimide bond or the triazole bond is attached to the aryl ring, and when Z is the 1,3-succinimide bond, N atom of the 1,3-succinimide bond is attached to the alkyl group connected to X, Y is thiol group (—SH), amine group (—NH$_2$), azido group (—N$_3$), carboxylic acid group (—COOH) or disulfide-contained group (—S—S—R$_2$), R$_2$ is pyridine

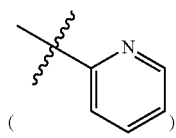 [SMILES: *c1ccccn1]

or 1,2-dithiolane-contained group

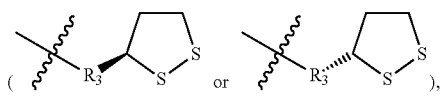

R$_3$ is methylene group (—CH$_2$—) or N—(3H-1,2,3,-triazo)4-methyl pentanamide

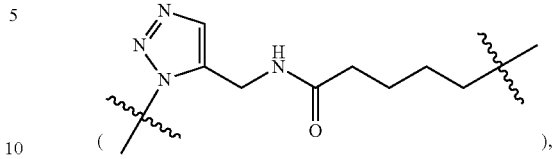

R$_4$ is hydrogen (H) or nitro group (—NO$_2$), m is an integral from 1 to 10, n is an integral from 0 to 10, and o is 1 or 2.

2. The borate moiety-contained linker of claim 1, when R$_1$ is

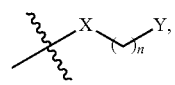

wherein n is an integral from 0 to 10,

X is ester bond (—COO— or —OCO—), 1,3-succinimide bond

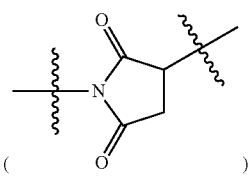 [SMILES: *C1CC(=O)N(*)C1=O]

or triazole bond

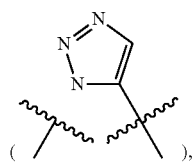

when X is the 1,3-succinimide bond or the triazole bond, N atom of the ring 1,3-succinimide bond or the triazole bond is attached to the aryl ring, and Y is thiol group (—SH), amine group (—NH$_2$), azido group (—N$_3$), carboxylic acid group (—COOH) or disulfide-contained group (—S—S—R$_2$), R$_2$ is pyridine

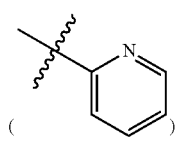

or 1,2-dithiolane-contained group

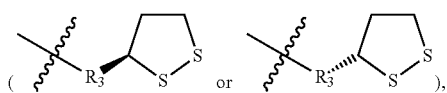

$R_3$ is methylene group ($-CH_2-$) or N—(3H-1,2,3-triazo-4-methyl pentanamide

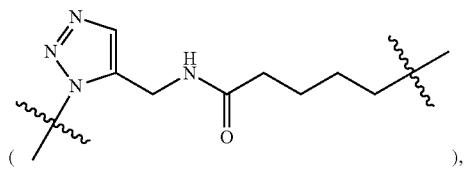 [SMILES: *CCCCC(=O)NCc1cnnn1*]

and
the compound is represented by the following chemical formula (II):

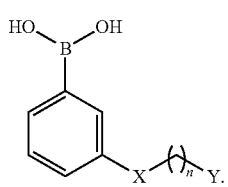
(II)

3. The borate moiety-contained linker of claim 1, when $R_1$ is

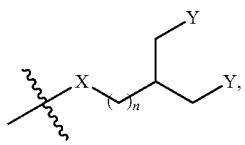

wherein
n is an integral from 0 to 10,
X is ester bond ($-COO-$ or $-OCO-$), 1,3-succinimide bond

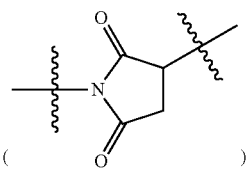 [SMILES: *C1CC(=O)N(*)C1=O]

or triazole bond

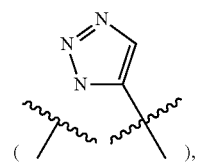

when X is the 1,3-succinimide bond or the triazole bond, N atom of the 1,3-succinimide bond or the triazole bond is attached to the aryl ring, and
Y is thiol group ($-SH$), amine group ($-NH_2$), azido group ($-N_3$), carboxylic acid group ($-COOH$) or disulfide-contained group ($-S-S-R_2$),
$R_2$ is pyridine

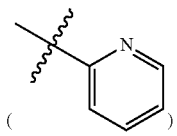

or 1,2-dithiolane-contained group

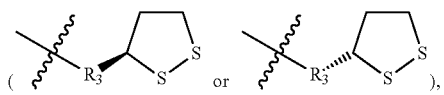

$R_3$ is methylene group ($-CH_2-$) or N—(3H-1,2,3,-triazo)-4-methyl pentanamide

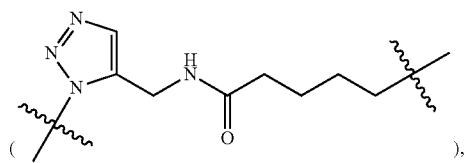 [SMILES: *CCCCC(=O)NCc1cnnn1*]

and
the compound is represented by the following chemical formula (III):

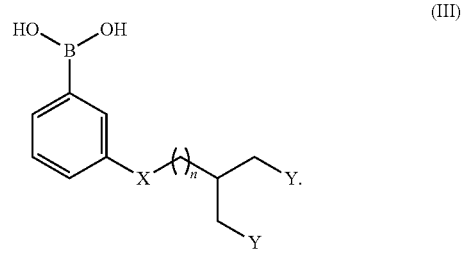
(III)

4. The borate moiety-contained linker of claim 1, wherein $R_1$ is

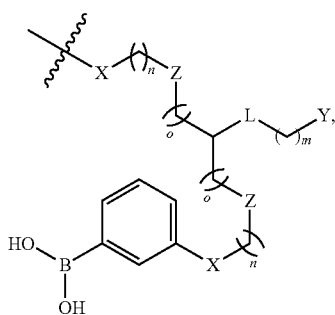

wherein m is an integral from 1 to 10, n is an integral from 0 to 10, o is 1 or 2, X is selected from the group consisting of ester bond (—COO— and —OCO—), 1,3-succinimide bond

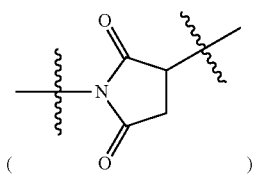

and triazole bond

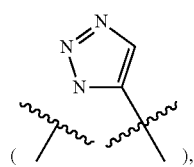

and L is ester bond (—COO— and —OCO—), and Z is selected from the group consisting of amide bond (—CONH— and —NHCO—), ester bond (—COO— and —OCO—), 1,3-succinimide bond

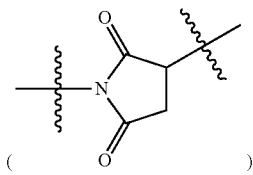

and triazole bond

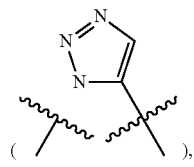

and X, Z and L are different to each other, and when X is the 1,3-succinimide bond or the triazole bond, N atom of the 1,3-succinimide bond or the triazole bond is attached to the aryl ring, and when Z is the 1,3-succinimide bond, N atom of the 1,3-succinimide bond is attached to the alkyl group connected to X, Y is thiol group (—SH), amine group (—NH$_2$), azido group (—N$_3$), carboxylic acid group (—COOH) or disulfide-contained group (—S—S—R$_2$), R$_2$ is pyridine

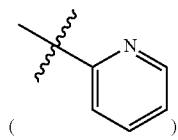 [SMILES: *c1ccccn1]

or 1,2-dithiolane-contained group

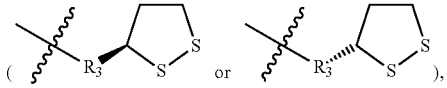

R$_3$ is N—(3H-1,2,3,-triazo)-4-methyl pentanamide

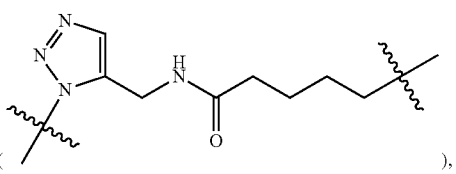

and the compound s represented by the following chemical formula (IV):

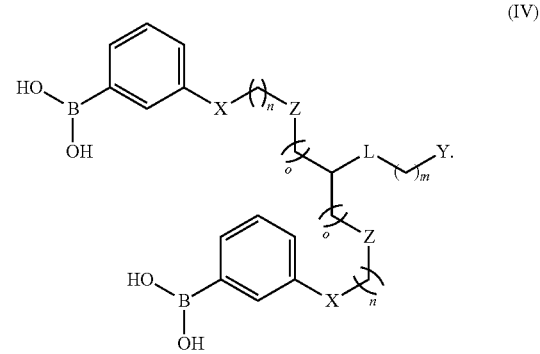

(IV)

5. The borate moiety-contained linker of claim 1, when R$_1$ is

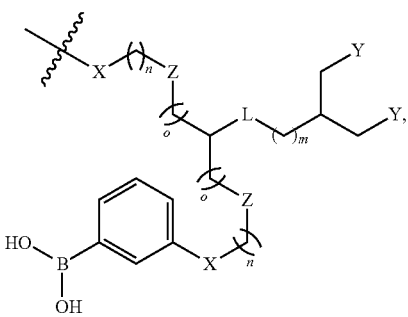

wherein m is an integral from 1 to 10, n is an integral from 0 to 10, o is 1 or 2, X is selected from the group consisting of ester bond (—COO— and —OCO—), 1,3-succinimide bond

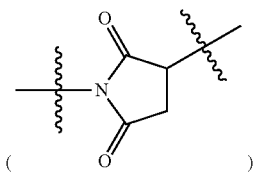 [SMILES: *C1CC(=O)N(*)C1=O]

and triazole bond

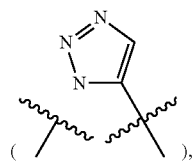

and L is ester bond (—COO— and —OCO—), and Z is selected from the group consisting of amide bond (—CONH— and —NHCO—), ester bond (—COO— and —OCO—), 1,3-succinimide bond

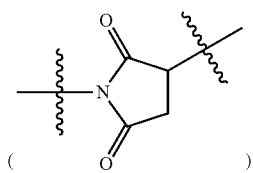 [SMILES: *C1CC(=O)N(*)C1=O]

and triazole bond

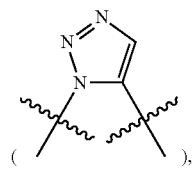

and X, Z and L are different to each other, and
when X is the 1,3-succinimide bond or the triazole bond, N atom of the 1,3-succinimide bond or the triazole bond is attached to the aryl ring, and
when Z is the 1,3-succinimide bond, N atom of the 1,3-succinimide bond is attached to the alkyl group connected to X,
Y is thiol group (—SH), amine group (—NH$_2$), azido group (—N$_3$), carboxylic acid group (—COOH) or disulfide-contained group (—S—S—R$_2$),
R$_2$ is pyridine

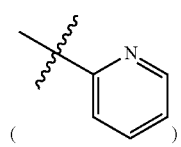 [SMILES: *c1ccccn1]

or 1,2-dithiolane-contained group

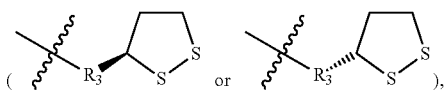

R$_3$ is methylene group (—CH$_2$—) or N—(3H-1,2,3,-triazo)-4-methyl pentanamide

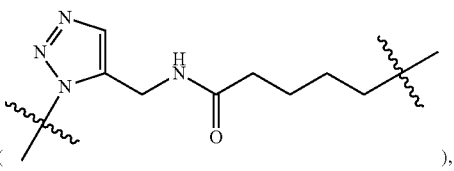

and
the compound is represented by the following chemical formula (V):

(V)

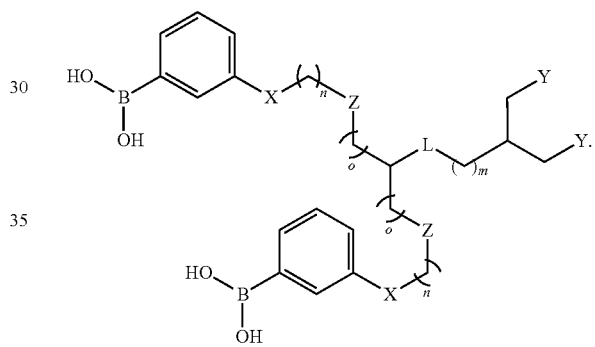

6. The borate moiety-contained linker of claim 1, when R$_1$ is

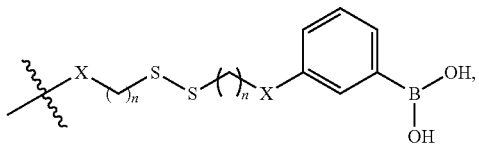

wherein
n is an integral from 0 to 10,
X is ester bond (—COO— or —OCO—), 1,3-succinimide bond

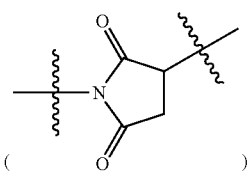

or triazole bond

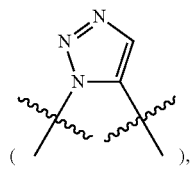

when X is the 1,3-succinimide bond or the triazole bond, N atom of the 1,3-succinimide bond or the triazole bond is attached to the aryl ring, and
the compound is represented by the following chemical formula (VI):

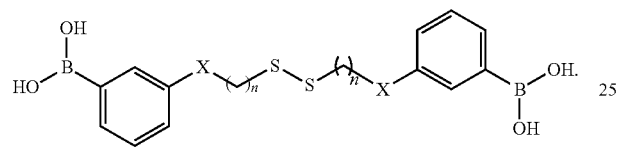

(VI)

7. The borate moiety-contained linker of claim 1, when $R_1$ is

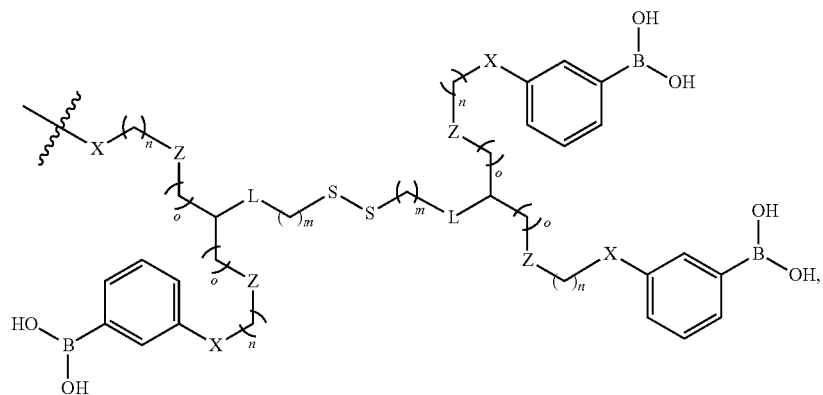

wherein
m is an integral from 1 to 10,
n is an integral from 0 to 10,
X is selected from the group consisting of ester bond (—COO— and —OCO—), 1,3-succinimide bond

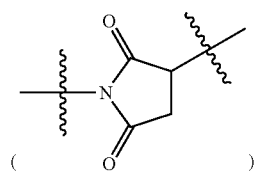 [SMILES: *C1CC(=O)N(*)C1=O]

and triazole bond

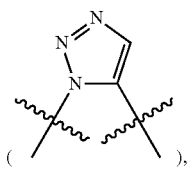

and L is ester bond (—COO— and —OCO—) and Z is selected from the group consisting of amide bond (—CONH— and —NHCO—), ester bond (—COO— and —OCO—), 1,3-succinimide bond

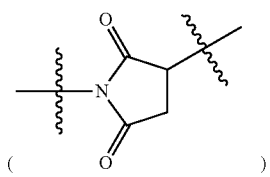

and triazole bond

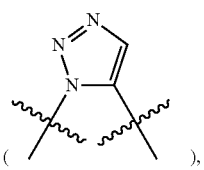 [SMILES: *c1cnnn1*]

and X, Z and L are different to each other, and
when X is the 1,3-succinimide bond or the triazole bond, N atom of the 1,3-succinimide bond or the triazole bond is attached to the aryl ring, and
when Z is the 1,3-succinimide bond, N atom of the 1,3-succinimide bond is attached to the alkyl group connected to X, and the compound is represented by the following chemical formula (VII):

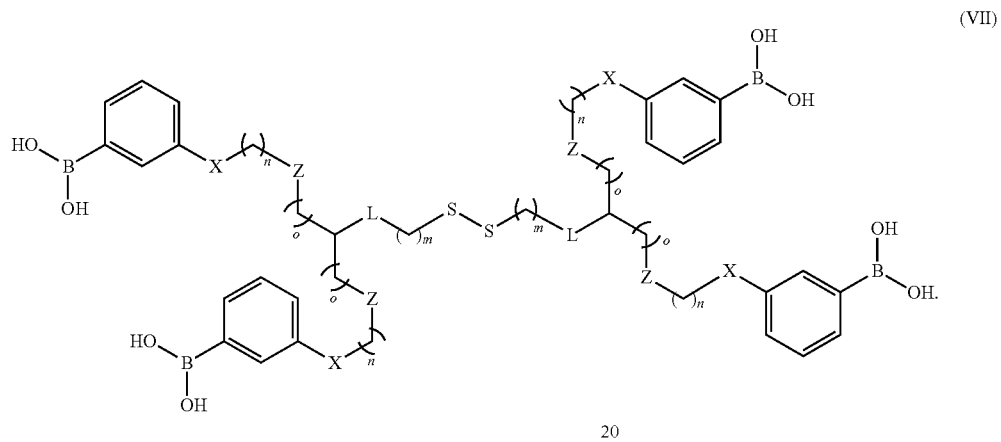

8. The borate moiety-contained linker of claim 1, when $R_1$ is

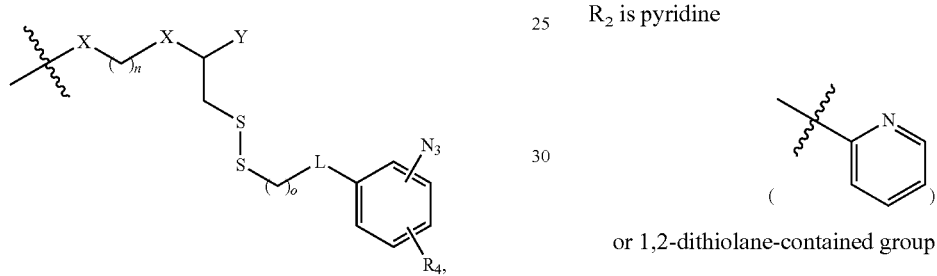

wherein
n is an integral from 0 to 10,
o is 1 or 2,
X is selected from the group consisting of ester bond (—COO— or —OCO—), 1,3-succinimide bond

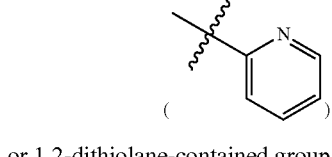

or triazole bond

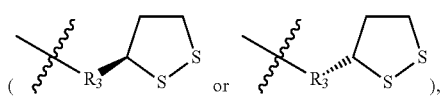

when X is the 1,3-succinimide bond or the triazole bond, N atom of the 1,3-succinimide bond or the triazole bond is attached to the aryl ring, and
L is ester bond (—COO— and —OCO—), and X and L are different to each other, Y is thiol group (—SH), amine group (—NH$_2$) azido group (—N$_3$), carboxylic acid group (—COOH) or disulfide-contained group (—S—S—R$_2$),
$R_2$ is pyridine

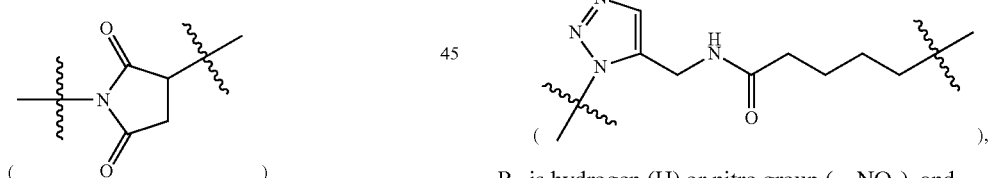

or 1,2-dithiolane-contained group

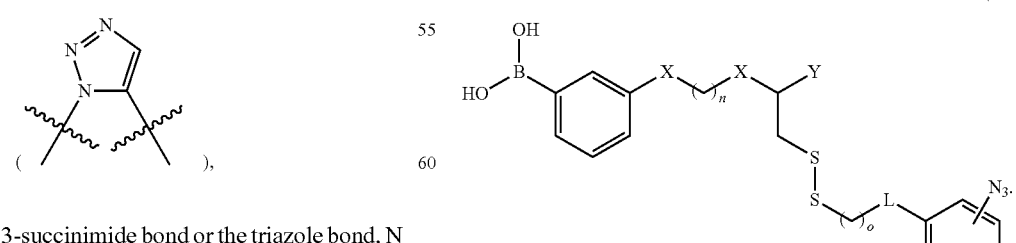

$R_3$ is methylene group (—CH$_2$—) or N—(3H-1,2,3,-triazo)-4-methyl pentanamid $R_4$ is hydrogen (H) or nitro group (—NO$_2$), and
the compound is represented by the following chemical formula (VIII):

(VIII)

9. The borate moiety-contained linker of claim 1, wherein $R_1$ is

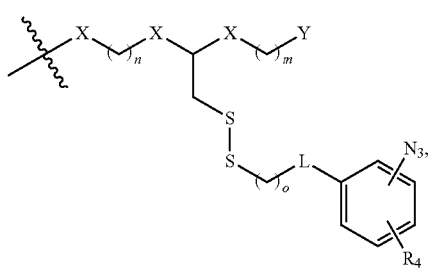

wherein
m is an integral from 1 to 10,
n is an integral from 0 to 10,
o is 1 or 2,
X is selected from the group consisting of ester bond (—COO— and —OCO—), 1,3-succinimide bond

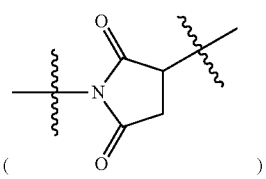

and triazole bond

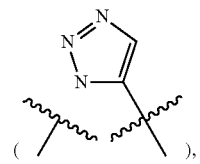

when X is the 1,3-succinimide bond or the triazole bond, N atom of the 1,3-succinimide bond or the triazole bond is attached to the aryl ring, and
L is ester bond (—COO— and —OCO—), and X and L are different to each other,
Y is thiol group (—SH), amine group (—NH$_2$), azido group (—N$_3$), carboxylic acid group (—COOH) or disulfide-contained group (—S—S—R$_2$), $R_2$ is pyridine

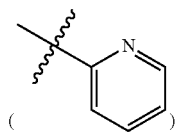 [SMILES: *c1ccccn1]

or 1,2-dithiolane-contained group

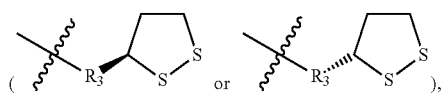

$R_3$ is methylene group (—CH$_2$—) or N—(3H-1,2,3,-triazo)-4-methyl pentanamide

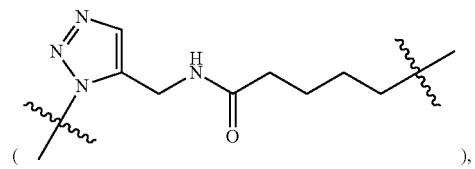

$R_4$ is hydrogen (H) or nitro group (—NO$_2$), and
the compound is represented by the following chemical formula (IX):

(IX)

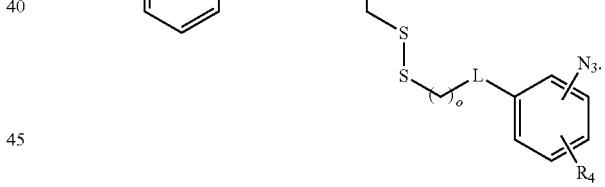

* * * * *